Figure 2:
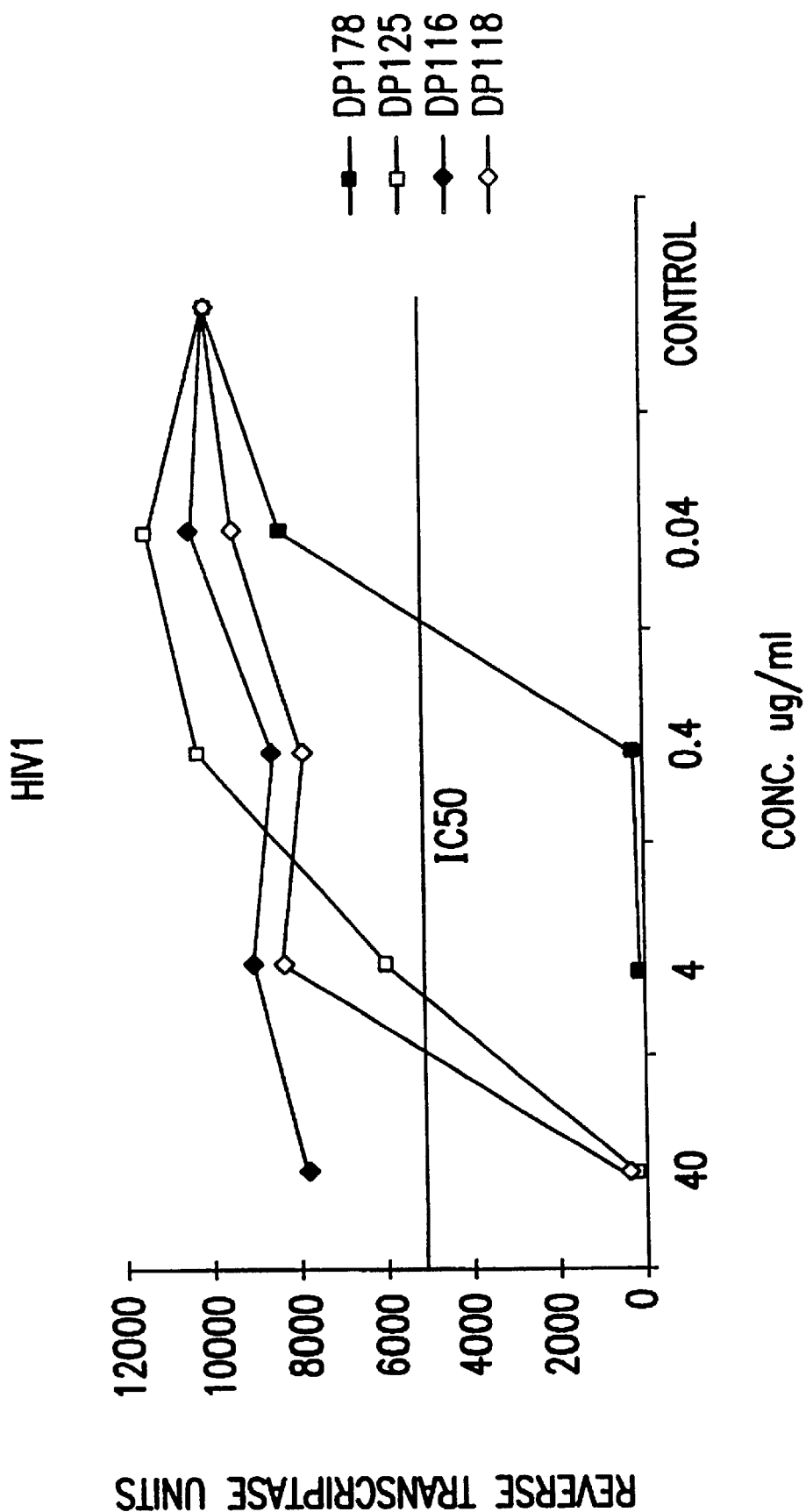

United States Patent [19]

Bolognesi et al.

[11] Patent Number: 6,133,418
[45] Date of Patent: *Oct. 17, 2000

[54] SYNTHETIC PEPTIDE INHIBITORS OF HIV TRANSMISSION

[75] Inventors: Dani Paul Bolognesi; Thomas James Matthews; Carl T. Wild, all of Durham, N.C.

[73] Assignee: Duke University, Durham, N.C.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/554,616

[22] Filed: Nov. 6, 1995

Related U.S. Application Data

[62] Division of application No. 08/073,028, Jun. 7, 1993, Pat. No. 5,464,933.

[51] Int. Cl.[7] ...................................................... A61K 38/00
[52] U.S. Cl. ............................ 530/324; 530/333; 435/974
[58] Field of Search .................................... 530/324–331, 530/333, 334; 435/974

[56] References Cited

FOREIGN PATENT DOCUMENTS

88/08429  11/1988  WIPO .
91/09872  of 1991  WIPO .

*Primary Examiner*—Jeffrey Stucker
*Attorney, Agent, or Firm*—Pennie & Edmonds LLP

[57] ABSTRACT

The present invention relates to peptides which exhibit potent anti-retroviral activity. The peptides of the invention comprise DP-178 (SEQ ID:1) ptide corresponding to amino acids 638 to 673 of the HIV-1$_{LAI}$ gp41 protein, and fragments, analogs and homologs of DP-178. The invention further relates to the uses of such peptides as inhibitory of human and non-human retroviral, especially HIV, transmission to uninfected cells.

3 Claims, 6 Drawing Sheets

HIV1LAI (DP-178; SEQ ID:1)   YTSLIHSLIEESQNQQEKNEQELLELDKWASLWNWF

HIV1SF2 (DP-185; SEQ ID:3)   YTNTIYTLLEESQNQQEKNEQELLELDKWASLWNWF

HIV1RF (SEQ ID:4)            YTGIIYNLLEESQNQQEKNEQELLELDKWANLWNWF

HIV1MN (SEQ ID:5)            YTSLIYSLLEKSQIQQEKNEQELLELDKWASLWNWF

HIV2ROD (SEQ ID:6)           LEANISKSLEQAQIQQEKNMYELQKLNSWDIFGNWF

HIV2NIHZ (SEQ ID:7)          LEANISQSLEQAQIQQEKNMYELQKLNSWDVFTNWL

DP180 (SEQ ID:2)             SSESFTLLEQWNNWKLQLAEQWLEQINEKHYLEDIS

DP118 (SEQ ID:10)            QQLLDVVKRQQEMLRLTVWGTKNLQARVTAIEKYLKDQ

DP125 (SEQ ID:8)             CGGNNLLRAIEAQQHLLQLTVWGIKQLQARILAVERYLKDQ

DP116 (SEQ ID:9)             LQARILAVERYLKDQQQ

FIG.1

| Number of Syncytia/well: | concentration in μg/ml (micrograms/ml) | | | | | | | | |
|---|---|---|---|---|---|---|---|---|---|
| DP178 | 10 | 5 | 1 | 0.2 | 0.1 | 0.05 | 0.025 | 0.0125 | Control |
| *Syncytia* | | | | | | | | | |
| HIV1LAI | 0 | 0 | 0 | 0 | 0 | 0 | 0 | 0 | 67 |
| HIV1MN | 0 | 0 | 0 | 0 | 0 | ND | ND | ND | 34 |
| HIV1RF | 0 | 0 | 0 | 0 | 0 | ND | ND | ND | 65 |
| HIV1SF2 | 0 | 0 | 0 | 0 | 0 | ND | ND | ND | 58 |
| | | | | | | | | | |
| DP125 | 10 | 5 | 1 | 0.2 | 0.1 | 0.05 | 0.025 | 0.0125 | Control |
| *Syncytia* | | | | | | | | | |
| HIV1LAI | 0 | 0 | 54 | 69 | 80 | 75 | 79 | 82 | 67 |
| HIV1MN | 0 | 0 | 30 | 36 | ND | ND | ND | ND | 34 |
| HIV1RF | 0 | 0 | 67 | 63 | ND | ND | ND | ND | 65 |
| HIV1SF2 | 0 | 0 | 9 | 66 | ND | ND | ND | ND | 58 |
| | | | | | | | | | |
| DP116 | 10 | 5 | 1 | 0.2 | 0.1 | 0.05 | 0.025 | 0.0125 | Control |
| *Syncytia* | | | | | | | | | |
| HIV1LAI | 75 | ND | ND | ND | ND | ND | ND | ND | 67 |
| HIV1MN | 35 | ND | ND | ND | ND | ND | ND | ND | 34 |
| HIV1RF | 81 | ND | ND | ND | ND | ND | ND | ND | 65 |
| HIV1SF2 | 81 | ND | ND | ND | ND | ND | ND | ND | 58 |

FIG.4A

| DP180 | 40 | 20 | 10 | 5 | 2.5 | 1.25 | 0.625 | 0.3125 | Control |
|---|---|---|---|---|---|---|---|---|---|
| *Syncytia* | | | | | | | | | |
| HIV1LAI | 50 | >45 | >45 | >45 | >45 | >45 | >45 | >45 | 58 |
| | | | | | | | | | |
| DP185 | 40 | 20 | 10 | 5 | 2.5 | 1.25 | 0.625 | 0.3125 | Control |
| *Syncytia* | | | | | | | | | |
| HIV1LAI | 0 | 0 | 0 | 0 | 0 | 0 | 0 | ND | 60 |

FIG.4B

HIV1

Number of Syncytia/well: concentration in ng/ml (nanograms/ml)

| DP178 Syncytia | 20 | 10 | 5 | 2.5 | 1.25 | 0.625 | 0.3125 | Control |
|---|---|---|---|---|---|---|---|---|
| HIV1 | 0 | 0 | 0 | 0 | 0 | 14 | 20 | 48 |

| DP116 Syncytia | 20 | 10 | 5 | 2.5 | 1.25 | 0.625 | 0.3125 | Control |
|---|---|---|---|---|---|---|---|---|
| HIV1 | ND | 48 | ND | ND | ND | ND | ND | ND |

HIV2

Number of Syncytia/well: concentration in µg/ml (micrograms/ml)

| DP178 Syncytia | 20 | 10 | 5 | 2.5 | 1.25 | 0.625 | 0.3125 | Control |
|---|---|---|---|---|---|---|---|---|
| HIV2 | 50 | 54 | 55 | 57 | 63 | 77 | 78 | 76 |

| DP116 Syncytia | 20 | 10 | 5 | 2.5 | 1.25 | 0.625 | 0.3125 | Control |
|---|---|---|---|---|---|---|---|---|
| HIV2 | ND | 58 | ND | ND | ND | ND | ND | ND |

FIG.5

SYNTHETIC PEPTIDE INHIBITORS OF HIV TRANSMISSION

This is a division of application Ser. No. 08/073,028, filed Jun. 7, 1993, U.S. Pat. No. 5,464,933.

TABLE OF CONTENTS
INTRODUCTION
BACKGROUND OF THE INVENTION
  2.1 THE HUMAN IMMUNODEFICIENCY VIRUS
  2.2 HIV TREATMENT
3. SUMMARY OF THE INVENTION
  3.1 DEFINITIONS
4. BRIEF DESCRIPTION OF THE FIGURES
5. DETAILED DESCRIPTION OF THE INVENTION
  5.1 DP-178 AND DP-178-LIKE PEPTIDES
  5.2 ASSAYS FOR ANTIVIRAL ACTIVITY
  5.3 USES OF THE PEPTIDES OF THE INVENTION
6. EXAMPLE: DP-178 (SEQ ID:1) IS A POTENT INHIBITOR OF HIV-1 INFECTION
  6.1 MATERIALS AND METHODS
    6.1.1. Peptide Synthesis
    6.1.2. Virus
    6.1.3. Cell Fusion Assay
    6.1.5. Reverse Transcriptase Assay
  6.2 RESULTS
    6.2.1. Peptide Inhibition of Infected Cell-Induced Syncytia Formation
    6.2.2. Peptide Inhibition of Infection by Cell-Free Virus

1. INTRODUCTION

The present invention relates to DP-178 (SEQ ID:1), a peptide corresponding to amino acids 638 to 673 of the HIV-$1_{LAI}$ transmembrane protein (TM) gp41, and portions, analogs, and homologs of DP-178 (SEQ ID:1), all of which exhibit anti-retroviral activity. Such anti-retroviral activity includes, but is not limited to, the inhibition of HIV transmission to uninfected CD-$4^+$ cells. Further, the invention relates to the use of DP-178 (SEQ ID:1) and DP-178 fragments and/or analogs or homologs as inhibitors of human and non-human retroviral, especially HIV, transmission to uninfected cells. Still further, the invention relates to the use of DP-178 as a HIV subtype-specific diagnostic. The invention is demonstrated by way of a working example wherein DP-178 (SEQ ID:1), and a peptide whose sequence is homologous to DP-178 are each shown to be potent, non-cytotoxic inhibitors of HIV-1 transfer to uninfected CD-$4^+$ cells.

2. BACKGROUND OF THE INVENTION
2.1 THE HUMAN IMMUNODEFICIENCY VIRUS

The human immunodeficiency virus (HIV) has been implicated as the primary cause of the slowly degenerative immune system disease termed acquired immune deficiency syndrome (AIDS) (Barre-Sinoussi, F. et al., 1983, Science 220:868–870; Gallo, R. et al., 1984, Science 224:500–503). there are at least two distinct types of HIV: HIV-1 (Barre-Sinoussi, F. et al., 1983, Science 220:868–870; Gallo R. et al., 1984, Science 224:500–503) and HIV-2 (Clavel, F. et al., 1986, Science 233:343–346; Guyader, M. et al., 1987, Nature 326:662–669). Further, a large amount of genetic heterogeneity exists within populations of each of these types. Infection of human CD-$4^+$ T-lymphocytes with an HIV virus leads to depletion of the cell type and eventually to opportunistic infections, neurological dysfunctions, neoplastic growth, and ultimately death.

HIV is a member of the lentivirus family of retroviruses (Teich, N. et al., 1984, RNA Tumor Viruses, Weiss, R. et al., eds., CSH-Press, pp. 949–956). Retroviruses are small enveloped viruses that contain a diploid, single-stranded RNA genome, and replicate via a DNA intermediate produced by a virally-encoded reverse transcriptase, an RNA-dependent DNA polymerase (Varmus, H., 1988, Science 240:1427–1439). Other retroviruses include, for example, oncogenic viruses such as human T-cell leukemia viruses (HTLV-I,-II,-III), and feline leukemia virus.

The HIV viral particle consists of a viral core, composed of capsid proteins, that contains the viral RNA genome and those enzymes required for early replicative events. Myristylated Gag protein forms an outer viral shell around the viral core, which is, in turn, surrounded by a lipid membrane envelope derived from the infected cell membrane. The HIV envelope surface glycoproteins are synthesized as a single 160 kD precursor protein which is cleaved by a cellular protease during viral budding into two glycoproteins, gp41 and gp120. gp41 is a transmembrane protein and gp120 is an extracellular protein which remains non-covalently associated with gp41, possibly in a trimeric or multimeric form (Hammarskjold, M. and Rekosh, D., 1989, Biochem. Biophys. Acta 989:269–280).

HIV is targeted to CD-$4^+$ cells because the CD-4 cell surface protein acts as the cellular receptor for the HIV-1 virus (Dalgleish, A. et al., 1984, Nature 312:763–767; Klatzmann et al., 1984, Nature 312:767–768; Maddon et al., 1986, Cell 47:333–348). Viral entry into cells is dependent upon gp120 binding the cellular CD-$4^+$ receptor molecules (McDougal, J. S. et al., 1986, Science 231:382–385; Maddon, P. J. et al., 1986, Cell 47:333–348) and thus explains HIV's tropism for CD-$4^+$ cells, while gp41 anchors the envelope glycoprotein complex in the viral membrane.

2.2 HIV TREATMENT

HIV infection is pandemic and HIV associated diseases represent a major world health problem. Although considerable effort is being put into the successful design of effective therapeutics, currently no curative anti-retroviral drugs against AIDS exist. In attempts to develop such drugs, several stages of the HIV life cycle have been considered as targets for therapeutic intervention (Mitsuya, H. et al., 1991, FASEB J. 5:2369–2381). For example, virally encoded reverse transcriptase has been one focus of drug development. A number of reverse-transcriptase-targeted drugs, including 2',3'-dideoxynucleoside analogs such as AZT, ddI, ddC, and d4T have been developed which have been shown to been active against HIV (Mitsuya, H. et al., 1991, Science 249:1533–1544). While beneficial, these nucleoside analogs are not curative, probably due to the rapid appearance of drug resistant HIV mutants (Lander, B. et al., 1989, Science 243:1731–1734). In addition, the drugs often exhibit toxic side effects such as bone marrow suppression, vomiting, and liver function abnormalities.

Attempts are also being made to develop drugs which can inhibit viral entry into the cell, the earliest stage of HIV infection. Here, the focus has thus far been on CD4, the cell surface receptor for HIV. Recombinant soluble CD4, for example, has been shown to inhibit infection of CD-$4^+$ T-cells by some HIV-1 strains (Smith, D. H. et al., 1987, Science 238:1704–1707). Certain primary HIV-1 isolates, however, are relatively less sensitive to inhibition by recombinant CD-4 (Daar, E. et al., 1990, Proc. Natl. Acad. Sci. USA 87:6574–6579). In addition, recombinant soluble CD-4 clinical trials have produced inconclusive results (Schooley, R. et al., 1990, Ann. Int. Med. 112:247–253; Kahn, J. O. et al., 1990, Ann. Int. Med. 112:254–261; Yarchoan, R. et al., 1989, Proc. Vth Int. Conf. on AIDS, p. 564, MCP 137).

The late stages of HIV replication, which involve crucial virus-specific secondary processing of certain viral proteins, have also been suggested as possible anti-HIV drug targets. Late stage processing is dependent on the activity of a viral protease, and drugs are being developed which inhibit this protease (Erickson, J., 1990, Science 249:527–533). The clinical outcome of these candidate drugs is still in question.

Attention is also being given to the development of vaccines for the treatment of HIV infection. The HIV-1 envelope proteins (gp160, gp120, gp41) have been shown to be the major antigens for anti-HIV antibodies present in AIDS patients (Barin, et al., 1985, Science 228:1094–1096). Thus far, therefore, these proteins seem to be the most promising candidates to act as antigens for anti-HIV vaccine development. To this end, several groups have begun to use various portions of gp160, gp120, and/or gp41 as immunogenic targets for the host immune system. See for example, Ivanoff, L. et al., U.S. Pat. No. 5,141,867; Saith, G. et al., WO 92/22,654; Shafferman, A., WO 91/09,872; Formoso, C. et al., WO 90/07,119. Clinical results concerning these candidate vaccines, however, still remain far in the future.

Thus, although a great deal of effort is being directed to the design and testing of anti-retroviral drugs, a truly effective, non-toxic treatment is still needed.

3. SUMMARY OF THE INVENTION

The present invention relates, first, to DP-178 (SEQ ID:1), a 36-amino acid synthetic peptide corresponding to amino acids 638 to 673 of the transmembrane protein (TM) gp41 from the HIV-1 isolate LAI, which exhibits potent anti-HIV-1 activity. As evidenced by the working example presented below, the DP-178 (SEQ ID:1) anti-viral activity is so high that, on a weight basis, no other known anti-HIV agent is effective at concentrations as low as those at which DP-178 (SEQ ID:1) exhibits its inhibitory effects. The invention further relates to those portions, analogs, and homologs of DP-178 which also show such antiviral activity. The antiviral activity of such DP-178 portions, analogs, and homologs, includes, but is not limited to the inhibition of HIV transmission to uninfected CD-4$^+$ cells. Finally, the invention relates to the use of DP-178 (SEQ ID:1) and DP-178 fragments and/or analogs or homologs. Such uses may include, but are not limited to, the use of the peptides as inhibitors of human and non-human retroviral, especially HIV, transmission to uninfected cells, and as type and/or subtype-specific diagnostic tools.

An embodiment of the invention is demonstrated below wherein an extremely low concentration of DP-178 (SEQ ID:1), and very low concentrations of a DP-178 homolog (SEQ ID:3) are shown to be potent inhibitors of HIV-1 mediated CD-4$^+$ cell-cell fusion (i.e., syncytial formation) and infection of CD-4$^+$ cells by cell-free virus. Further, it is shown that DP-178 (SEQ ID:1) is not toxic to cells, even at concentrations 3 logs higher than the inhibitory DP-178 (SEQ ID:1) concentration.

3.1 DEFINITIONS

Peptides are defined herein as organic compounds comprising two or more amino acids covalently joined by peptide bonds. Peptides may be referred to with respect to the number of constituent amino acids, i.e., a dipeptide contains two amino acid residues, a tripeptide contains three, etc. Peptides containing ten or fewer amino acids may be referred to as oligopeptides, while those with more than ten amino acid residues are polypeptides.

Peptide sequences defined herein are represented by one-letter symbols for amino acid residues as follows:
A (alanine)
R (arginine)
N (asparagine)
D (aspartic acid)
C (cysteine)
Q (glutamine)
E (glutamic acid)
G (glycine)
H (histidine)
I (isoleucine)
L (leucine)
K (lysine)
M (methionine)
F (phenylalanine)
P (proline)
S (serine)
T (threonine)
W (tryptophan)
Y (tyrosine)
V (valine)

4. BRIEF DESCRIPTION OF THE FIGURES

FIG. 1. Amino acid sequence of DP-178 (SEQ ID:1) derived from HIV$_{LAI}$; DP-178 homologs derived from HIV-1$_{SF2}$ (DP-185; (SEQ ID:3), HIV-1$_{RF}$ (SEQ ID:4), and HIV-1$_{MN}$ (SEQ ID:5); DP-178 homologs derived from amino acid sequences of two prototypic HIV-2 isolates, namely, HIV-2$_{rod}$ (SEQ ID:6) and HIV-2$_{NIHZ}$ (SEQ ID:7); control peptides: DP-180 (SEQ ID:2), a peptide incorporating the amino acid residues of DP-178 in a scrambled sequence; DP-118 (SEQ ID:10) unrelated to DP-178, which inhibits HIV-1 cell free virus infection; DP-125 (SEQ ID:8), unrelated to DP-178, was also previously shown to inhibit HIV-1 cell free virus infection (Wild et al., 1992, Proc. Natl. Acad. Sci USA 89:10,537–10,541); DP-116 (SEQ ID:9), unrelated to DP-178 had previously been shown to be negative for inhibition of HIV-1 infection using the cell-free virus infection assay (Wild, et al., 1992, Proc. Natl. Acad. Sci USA 89:10,537–10,541). One letter amino acid code is used.

FIG. 2. Inhibition of HIV-1 cell-free virus infection by synthetic peptides. IC50 refers to the concentration of peptide that inhibits RT production from infected cells by 50% compared to the untreated control. Control: the level of RT produced by untreated cell cultures infected with the same level of virus as treated cultures.

Figure 3:
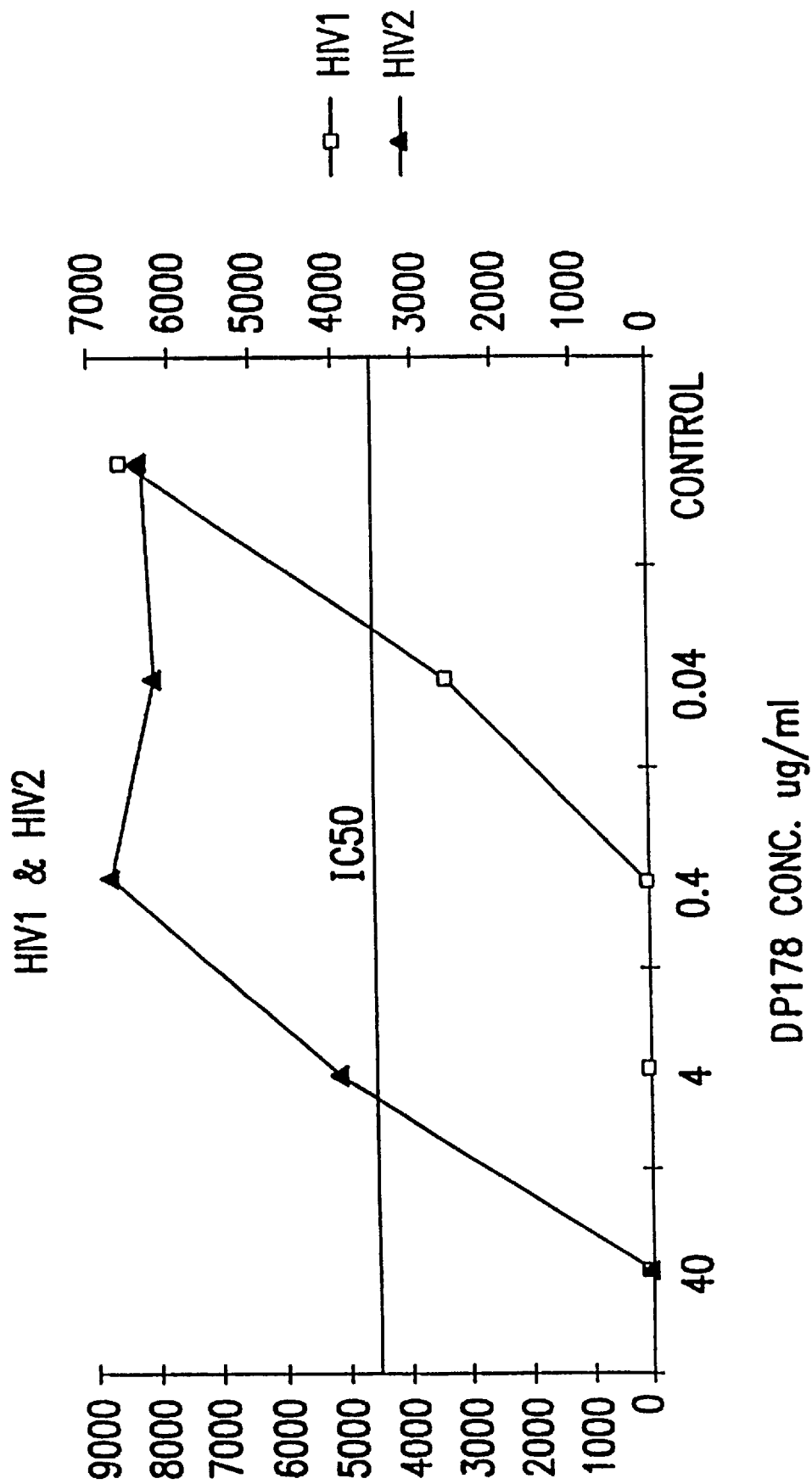

FIG. 3. Inhibition of HIV-1 and HIV-2 cell-free virus infection by the synthetic peptide DP-178 (SEQ ID:1). IC50: concentration of peptide that inhibits RT production by 50% compared to the untreated control. Control: Level of RT produced by untreated cell cultures infected with the same level of virus as treated cultures.

FIGS. 4A and 4B. Fusion Inhibition Assays. FIG. 4A represents DP-178 (SEQ. ID:1) inhibition of HIV-1 prototypic isolate-mediated synetia formation. Date represents the number of virus-induced syncytia per cell. FIG. 4B represents DP-185 (SEQ ID:3), a DP-178 homology derived from HIV-1$_{SF2}$ isolate, inhibition of syncytia formation. DP-180 (SEQ ID:2) represents a scrambled control peptide. Control represents number of syncytia produced in the absence of peptide.

FIG. 5. Fusion inhibition assay: HIV-1 vs. HIV-2. Data represents the number of virus-induced syncytia per well. ND: not done.

Figure 6:
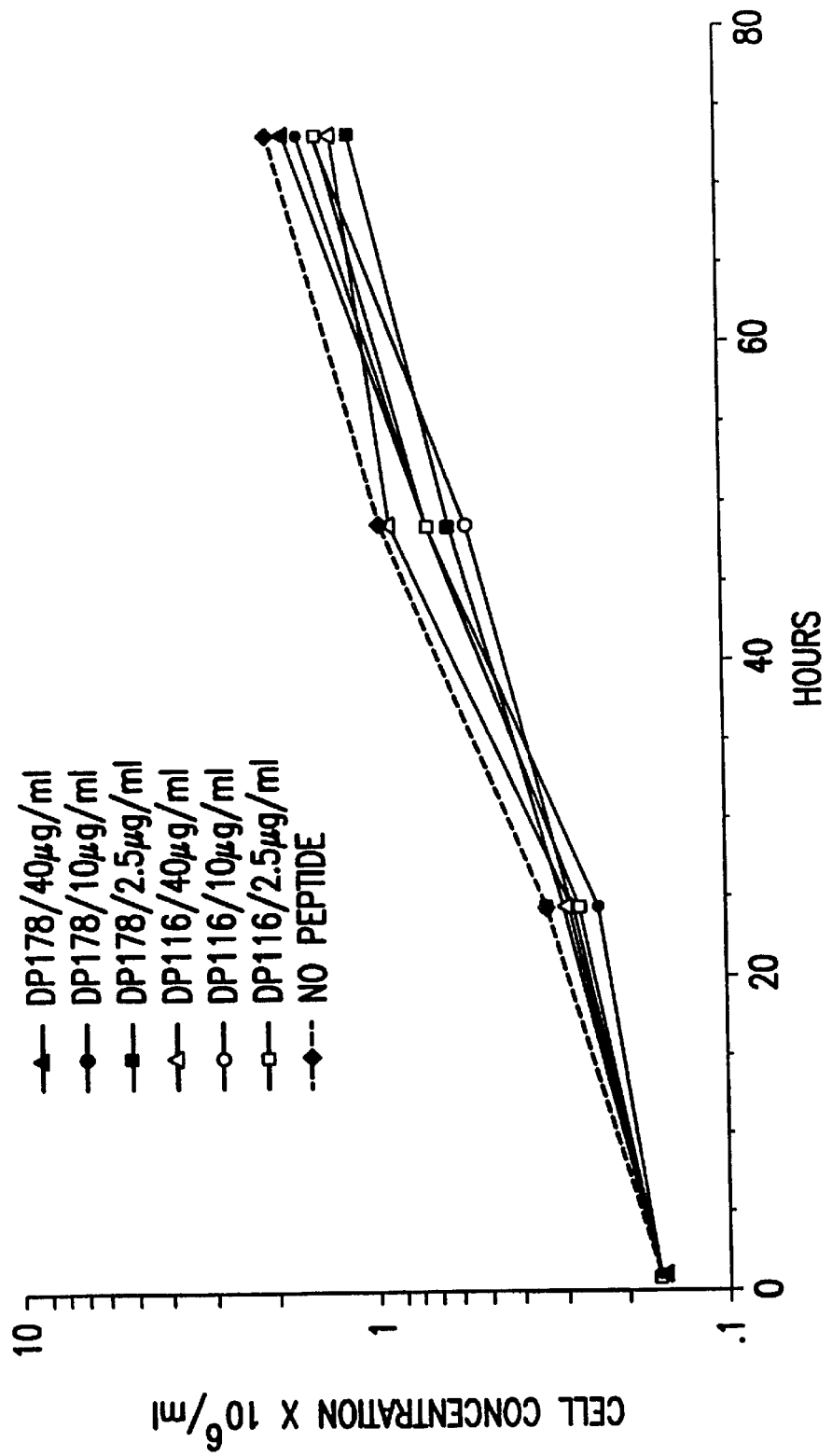

FIG. 6. Cytotoxicity study of DP-178 (SEQ ID:1) and DP-116 (SEQ ID:9) on CEM cells. Cell proliferation data is shown.

5. DETAILED DESCRIPTION OF THE INVENTION

Described herein are peptides that exhibit potent antiviral activity. These peptides include DP-178 (SEQ ID:1), a gp41-derived 36 amino acid peptide, fragments and/or analogs of DP-178, and peptides which are homologous to DP-178. Also described here are assays for testing the antiviral activities of such peptides. Finally, the use of the peptides of the invention as inhibitors of non-human and human retroviral, especially HIV, transmission are detailed, as is the use of the peptides as diagnostic indicators of the presence of specific retroviruses.

5.1 DP-178 AND DP-178-LIKE PEPTIDES

The peptide DP-178 (SEQ ID:1) of the invention corresponds to amino acid residues 638 to 673 of the transmembrane protein gp41 from the HIV-1$_{LAI}$ isolate, and has the 36 amino acid sequence (Reading from amino to carboxy terminus):

NH$_2$-YTSLIHSLIEESQNQQEKNEQELLELDKWASLWNWF-COOH  (SEQ ID:1)

In addition to the full-length DP-178 (SEQ ID:1) 36-mer, the peptides of the invention may include truncations of the DP-178 (SEQ ID:1) peptide which exhibit antiviral activity. Such truncated DP-178 (SEQ ID:1) peptides may comprise peptides of between 3 and 36 amino acid residues (i.e., peptides ranging in size from a tripeptide to a 36-mer polypeptide), and may include but are not limited to those listed in Tables I and II, below. Peptide sequences in these tables are listed from amino (left) to carboxy (right) terminus. "X" may represent an amino group (—NH$_2$) and "Z" may represent a carboxyl (—COOH) group. Alternatively, as described below, "X" and/or "Z" may represent a hydrophobic group, an acetyl group, a FMOC group, an amido group, or a covalently attached macromolecule.

TABLE I

DP-178 (SEQ ID:1) CARBOXY TRUNCATIONS

X-YTS-Z
X-YTSL-Z
X-YTSLI-Z
X-YTSLIH-Z
X-YTSLIHS-Z
X-YTSLIHSL-Z
X-YTSLIHSLI-Z
X-YTSLIHSLIE-Z
X-YTSLIHSLIEE-Z
X-YTSLIHSLIEES-Z
X-YTSLIHSLIEESQ-Z
X-YTSLIHSLIEESQN-Z
X-YTSLIHSLIEESQNQ-Z
X-YTSLIHSLIEESQNQQ-Z
X-YTSLIHSLIEESQNQQE-Z
X-YTSLIHSLIEESQNQQEK-Z
X-YTSLIHSLIEESQNQQEKN-Z
X-YTSLIHSLIEESQNQQEKNE-Z
X-YTSLIHSLIEESQNQQEKNEQ-Z

TABLE I-continued

DP-178 (SEQ ID:1) CARBOXY TRUNCATIONS

X-YTSLIHSLIEESQNQQEKNEQE-Z
X-YTSLIHSLIEESQNQQEKNEQEL-Z
X-YTSLIHSLIEESQNQQEKNEQELL-Z
X-YTSLIHSLIEESQNQQEKNEQELLE-Z
X-YTSLIHSLIEESQNQQEKNEQELLEL-Z
X-YTSLIHSLIEESQNQQEKNEQELLELD-Z
X-YTSLIHSLIEESQNQQEKNEQELLELDK-Z
X-YTSLIHSLIEESQNQQEKNEQELLELDKW-Z
X-YTSLIHSLIEESQNQQEKNEQELLELDKWA-Z
X-YTSLIHSLIEESQNQQEKNEQELLELDKWAS-Z
X-YTSLIHSLIEESQNQQEKNEQELLELDKWASL-Z
X-YTSLIHSLIEESQNQQEKNEQELLELDKWASLW-Z
X-YTSLIHSLIEESQNQQEKNEQELLELDKWASLWN-Z
X-YTSLIHSLIEESQNQQEKNEQELLELDKWASLWNW-Z
X-YTSLIHSLIEESQNQQEKNEQELLELDKWASLWNWF-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE II

DP-178 (SEQ ID:1) AMINO TRUNCATIONS

X-NWF-Z
X-WNWF-Z
X-LWNWF-Z
X-SLWNWF-Z
X-ASLWNWF-Z
X-WASLWNWF-Z
X-KWASLWNWF-Z
X-DKWASLWNWF-Z
X-LDKWASLWNWF-Z
X-ELDKWASLWNWF-Z
X-LELDKWASLWNWF-Z
X-LLELDKWASLWNWF-Z
X-ELLELDKWASLWNWF-Z

TABLE II-continued

DP-178 (SEQ ID:1) AMINO TRUNCATIONS

X-QELLELDKWASLWNWF-Z

X-EQELLELDKWASLWNWF-Z

X-NEQELLELDKWASLWNWF-Z

X-KNEQELLELDKWASLWNWF-Z

X-EKNEQELLELDKWASLWNWF-Z

X-QEKNEQELLELDKWASLWNWF-Z

X-QQEKNEQELLELDKWASLWNWF-Z

X-NQQEKNEQELLELDKWASLWNWF-Z

X-QNQQEKNEQELLELDKWASLWNWF-Z

X-SQNQQEKNEQELLELDKWASLWNWF-Z

X-ESQNQQEKNEQELLELDKWASLWNWF-Z

X-EESQNQQEKNEQELLELDKWASLWNWF-Z

X-IEESQNQQEKNEQELLELDKWASLWNWF-Z

X-LIEESQNQQEKNEQELLELDKWASLWNWF-Z

X-SLIEESQNQQEKNEQELLELDKWASLWNWF-Z

X-HSLIEESQNQQEKNEQELLELDKWASLWNWF-Z

X-IHSLIEESQNQQEKNEQELLELDKWASLWNWF-Z

X-LIHSLIEESQNQQEKNEQELLELDKWASLWNWF-Z

X-SLIHSLIEESQNQQEKNEQELLELDKWASLWNWF-Z

X-TSLIHSLIEESQNQQEKNEQELLELDKWASLWNWF-Z

X-YTSLIHSLIEESQNQQEKNEQELLELDKWASLWNWF-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl group; a macromolecular carrier group including but no limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

The antiviral peptides of the invention also include analogs of DP-178 and/or DP-178 truncations which may include, but are not limited to, peptides comprising the DP-178 (SEQ ID:1) sequence, or DP-178 truncated sequence, containing one or more amino acid substitutions, insertions and/or deletions. Analogs of DP-178 homologs, described below, are also within the scope of the invention. The DP-178 analogs of the invention exhibit antiviral activity, and may, further, possess additional advantageous features, such as, for example, increased bioavailability, and/or stability, or reduced host immune recognition.

HIV-1 and HIV-2 envelope proteins are structurally distinct, but there exists a striking amino acid conservation within the DP-178-corresponding regions of HIV-1 and HIV-2. The amino acid conservation is of a periodic nature, suggesting some conservation of structure and/or function. Therefore, one possible class of amino acid substitutions would include those amino acid changes which are predicted to stabilize the structure of the DP-178 peptides of the invention.

Amino acid substitutions may be of a conserved or non-conserved nature. Conserved amino acid substitutions consist of replacing one or more amino acids of the DP-178 (SEQ ID:1) peptide sequence with amino acids of similar charge, size, and/or hydrophobicity characteristics, such as, for example, a glutamic acid (E) to aspartic acid (D) amino acid substitution. When only conserved substitutions are made, the resulting peptide is functionally equivalent to DP-178 (SEQ ID:1) or the DP-178 peptide from which it is derived. Non-conserved substitutions consist of replacing one or more amino acids of the DP-178 (SEQ ID:1) peptide sequence with amino acids possessing dissimilar charge, size, and/or hydrophobicity characteristics, such as, for example, a glutamic acid (E) to valine (V) substitution.

Amino acid insertions may consist of single amino acid residues or stretches of residues ranging from 2 to 15 amino acids in length. One or more insertions may be introduced into DP-178 (SEQ ID:1), DP-178 fragments, analogs and/or DP-178 homologs (described below).

Deletions of DP-178 (SEQ ID:1), DP-178 fragments, analogs, and/or DP-178 homologs (described below) are also within the scope of the invention. Such deletions consist of the removal of one or more amino acids from the DP-178 or DP-178-like peptide sequence, with the lower limit length of the resulting peptide sequence being 4 to 6 amino acids. Such deletions may involve a single contiguous or greater than one discrete portion of the peptide sequences.

The peptides of the invention may further include homologs of DP-178 (SEQ ID:1) and/or DP-178 truncations which exhibit antiviral activity. Such DP-178 homologs are peptides whose amino acid sequences are comprised of the amino acid sequences of peptide regions of other (i.e., other than HIV-$1_{LAI}$) viruses that correspond to the gp41 peptide region from which DP-178 (SEQ ID:1) was derived. Such viruses may include, but are not limited to, other HIV-1 isolates and HIV-2 isolates. DP-178 homologs derived from the corresponding gp41 peptide region of other (i.e., non HIV-$1_{LAI}$) HIV-1 isolates may include, for example, peptide sequences as shown below.

NH$_2$-YT<u>NTIYTL</u>LEESQNQQEKNEQELLELDKWASLWNWF-COOH     (DP-185: SEQ ID:3);

NH$_2$-YT<u>GIIYNI</u>LEESQNQQEKNEQELLELDKWA<u>NL</u>WNWF—COOH     (SEQ ID:4);

NH$_2$-YTSL<u>IY</u>SL<u>LE</u>KSQIQQEKNEQELLELDKWASLWNWF-COOH (SEQ ID:5).

SEQ ID:3 (DP-185), SEQ ID:4, and SEQ ID:5 are derived from HIV-$1_{SF2}$, HIV-$1_{RF}$, and HIV-$1_{MN}$ isolates, respectively. Underlined amino acid residues refer to those residues that differ from the corresponding position in the DP-178 (SEQ ID:1) peptide. One such DP-178 homolog, DP-185 (SEQ ID:3), is described in the Working Example presented in Section 6, below, where it is demonstrated that DP-185 (SEQ ID:3) exhibits antiviral activity. The DP-178 homologs of the invention may also include truncations, amino acid substitutions, insertions, and/or deletions, as described above.

In addition, striking similarities, as shown in FIG. 1, exist within the regions of HIV-1 and HIV-2 isolates which correspond to the DP-178 sequence. A DP-178 homolog derived from the HIV-$2_{NIHZ}$ isolate has the 36 amino acid sequence (reading from amino to carboxy terminus):

NH$_2$-LEANISQSLEQAQIQQEKNMYELQKLNSWDVFTNWL-COOH (SEQ ID:7)

Table III and Table IV show some possible truncations of the HIV-2$_{NIHZ}$ DP-178 homolog, which may comprise peptides of between 3 and 36 amino acid residues (i.e., peptides ranging in size from a tripeptide to a 36-mer polypeptide). Peptide sequences in these tables are listed from amino (left) to carboxy (right) terminus. "X" may represent an amino group (—NH$_2$) and "Z" may represent a carboxyl (—COOH) group. Alternatively, as described below, "X" and/or "Z" may represent a hydrophobic group, an acetyl group, a FMOC group, an amido group, or a covalently attached macromolecule, as described below.

TABLE III

| HIV-$2_{NIHZ}$ DP-178 homolog carboxy truncations. |
|---|
| X-LEA-Z |
| X-LEAN-Z |
| X-LEANI-Z |
| X-LEANIS-Z |
| X-LEANISQ-Z |
| X-LEANISQS-Z |
| X-LEANISQSL-Z |
| X-LEANISQSLE-Z |
| X-LEANISQSLEQ-Z |
| X-LEANISQSLEQA-Z |
| X-LEANISQSLEQAQ-Z |
| X-LEANISQSLEQAQI-Z |
| X-LEANISQSLEQAQIQ-Z |
| X-LEANISQSLEQAQIQQ-Z |
| X-LEANISQSLEQAQIQQE-Z |
| X-LEANISQSLEQAQIQQEK-Z |
| X-LEANISQSLEQAQIQQEKN-Z |
| X-LEANISQSLEQAQIQQEKNM-Z |
| X-LEANISQSLEQAQIQQEKNMY-Z |
| X-LEANISQSLEQAQIQQEKNMYE-Z |
| X-LEANISQSLEQAQIQQEKNMYEL-Z |
| X-LEANISQSLEQAQIQQEKNMYELQ-Z |
| X-LEANISQSLEQAQIQQEKNMYELQK-Z |
| X-LEANISQSLEQAQIQQEKNMYELQKL-Z |
| X-LEANISQSLEQAQIQQEKNMYELQKLN-Z |
| X-LEANISQSLEQAQIQQEKNMYELQKLNS-Z |
| X-LEANISQSLEQAQIQQEKNMYELQKLNSW-Z |
| X-LEANISQSLEQAQIQQEKNMYELQKLNSWD-Z |
| X-LEANISQSLEQAQIQQEKNMYELQKLNSWDV-Z |
| X-LEANISQSLEQAQIQQEKNMYELQKLNSWDVF-Z |

TABLE III-continued

| HIV-$2_{NIHZ}$ DP-178 homolog carboxy truncations. |
|---|
| X-LEANISQSLEQAQIQQEKNMYELQKLNSWDVFT-Z |
| X-LEANISQSLEQAQIQQEKNMYELQKLNSWDVFTN-Z |
| X-LEANISQSLEQAQIQQEKNMYELQKLNSWDVFTNW-Z |
| X-LEANISQSLEQAQIQQEKNMYELQKLNSWDVFTNWL-Z |

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE IV

| HIV-$2_{ROD}$ DP-178 homolog amino truncations. |
|---|
| X-NWL-Z |
| X-TNWL-Z |
| X-FTNWL-Z |
| X-VFTNWL-Z |
| X-DVFTNWL-Z |
| X-WDVFTNWL-Z |
| X-SWDVFTNWL-Z |
| X-NSWDVFTNWL-Z |
| X-LNSWDVFTNWL-Z |
| X-KLNSWDVFTNWL-Z |
| X-QKLNSWDVFTNWL-Z |
| X-LQKLNSWDVFTNWL-Z |
| X-ELQKLNSWDVFTNWL-Z |
| X-YELQKLNSWDVFTNWL-Z |
| X-MYELQKLNSWDVFTNWL-Z |
| X-NMYELQKLNSWDVFTNWL-Z |
| X-KNMYELQKLNSWDVFTNWL-Z |
| X-EKNMYELQKLNSWDVFTNWL-Z |
| X-QEKNMYELQKLNSWDVFTNWL-Z |
| X-QQEKNMYELQKLNSWDVFTNWL-Z |
| X-IQQEKNMYELQKLNSWDVFTNWL-Z |
| X-QIQQEKNMYELQKLNSWDVFTNWL-Z |
| X-AQIQQEKNMYELQKLNSWDVFTNWL-Z |
| X-QAQIQQEKNMYELQKLNSWDVFTNWL-Z |

TABLE IV-continued

HIV-2_{ROD} DP-178 homolog amino truncations.

X-EQAQIQQEKNMYELQKLNSWDVFTNWL-Z

X-LEQAQIQQEKNMYELQKLNSWDVFTNWL-Z

X-SLEQAQIQQEKNMYELQKLNSWDVFTNWL-Z

X-QSLEQAQIQQEKNMYELQKLNSWDVFTNWL-Z

X-SQSLEQAQIQQEKNMYELQKLNSWDVFTNWL-Z

X-ISQSLEQAQIQQEKNMYELQKLNSWDVFTNWL-Z

X-NISQSLEQAQIQQEKNMYELQKLNSWDVFTNWL-Z

X-ANISQSLEQAQIQQEKNMYELQKLNSWDVFTNWL-Z

X-EANISQSLEQAQIQQEKNMYELQKLNSWDVFTNWL-Z

X-LEANISQSLEQAQIQQEKNMYELQKLNSWDVFTNWL-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

The peptides of the invention may be synthesized or prepared by techniques well known in the art. See, for example, Creighton, 1983, Proteins: Structures and Molecular Principles, W. H. Freeman and Co., N.Y., which is incorporated herein by reference in its entirety. Short peptides, for example, can be synthesized on a solid support or in solution. Longer peptides amy be made using recombinant DNA techniques. Here, the nucleotide sequences encoding the peptides of the invention may be synthesized, and/or cloned, and expressed according to techniques well known to those of ordinary skill in the art. See, for example, Sambrook, et al., 1989, Molecular Cloning, A Laboratory Manual, Vols. 1–3, Cold Spring Harbor Press, N.Y.

The peptides of the invention may alternatively be synthesized such that one or more of the bonds which link the amino acid residues of the peptides are non-peptide bonds. These alternative non-peptide bonds may be formed by utilizing reactions well known to those in the art, and may include, but are not limited to imino, ester, hydrazide, semicarbazide, and azo bonds, to name but a few. In yet another embodiment of the invention, peptides comprising the sequences described above may be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to the peptides' amino termini. Likewise, an acetyl group or a 9-fluorenylmethoxy-carbonyl group may be placed at the peptides' amino termini. (See "X" in Tables I to IV, above.) Additionally, the hydrophobic group, t-butyloxycarbonyl, or an amino group may be added to the peptides' carboxy termini. (See "Z" in Tables I to IV, above.) Further, the peptides of the invention may be synthesized such that their steric configuration is altered. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or inhibitory action of the peptides of the invention.

Any of the peptides described above may, additionally, have a non-peptide macromolecular carrier group covalently attached to their amino and/or carboxy termini. Such macromolecular carrier groups may include, for example, lipid-fatty acid conjugates, polyethylene glycol, or carbohydrates. "X", in Tables I to IV, above, may therefore additionally represent any of the above macromolecular carrier groups covalently attached to the amino terminus of a peptide. Likewise, "Z", in Tables I to IV, may additionally represent any of the macromolecular carrier groups described above.

5.2 ASSAYS FOR ANTIVIRAL ACTIVITY

The antiviral activity exhibited by the peptides of the invention may be measured, for example, by easily performed in vitro assays, such as those described below, which can test the peptides' ability to inhibit syncytia formation, or their ability to inhibit infection by cell-free virus. Using these assays, such parameters as the relative antiviral activity of the peptides, exhibit against a given strain of virus and/or the strain specific inhibitory activity of the peptide can be determined. A cell fusion assay may be utilized to test the peptides' ability to inhibit HIV-induced syncytia formation in vitro. Such an assay may comprise culturing uninfected CD-4$^+$ cells (such as Molt or CEM cells, for example) in the presence of chronically HIV-infected cells and a peptide to be assayed. For each peptide, a range of peptide concentrations may be tested. This range should include a control culture wherein no peptide has been added. Standard conditions for culturing, well known to those of ordinary skill in the art, are used. After incubation for an appropriate period (24 hours at 37° C., for example) the culture is examined microscopically for the presence of multinucleated giant cells, which are indicative of cell fusion and syncytia formation.

A reverse transcriptase (RT) assay may be utilized to test the peptides' ability to inhibit infection of CD-4$^+$ cells by cell-free HIV. Such an assay may comprise culturing an appropriate concentration (i.e., TCID$_{50}$) of virus and CD-4$^+$ cells in the presence of the peptide to be tested. Culture conditions well known to those in the art are used. As above, a range of peptide concentrations may be used, in addition to a control culture wherein no peptide has been added. After incubation for an appropriate period (e.g., 7 days) of culturing, a cell-free supernatant is prepared, using standard procedures, and tested for the present of RT activity as a measure of successful infection. The RT activity may be tested using standard techniques such as those described by, for example, Goff et al. (Goff, S. et al., 1981, J. Virol. 38:239–248) and/or Willey et al. (Willey, R. et al., 1988, J. Virol. 62:139–147). These references are incorporated herein by reference in their entirety.

5.3 USES OF THE PEPTIDES OF THE INVENTION

The peptides of the invention, i.e., DP-178 (SEQ ID:1), and DP-178 fragments, analogs, and homologs, exhibit potent antiviral activity. As such, the peptides may be used as inhibitors of human and non-human retroviral, especially HIV, transmission to uninfected cells. The human retroviruses whose transmission may be inhibited by the peptides of the invention include, but are not limited to all strains of HIV-1 and HIV-2 and the human T-lymphocyte viruses (HTLV-I, II, III). The non-human retroviruses whose transmission may be inhibited by the peptides of the invention include, but are not limited to bovine leukosis virus, feline sarcoma and leukemia viruses, simian sarcoma and leukemia viruses, and sheep progress pneumonia viruses.

With respect to HIV, the peptides of the invention may be used as a therapeutic in the treatment of AIDS. The peptides of the invention may be administered using techniques well known to those in the art. Preferably, agents are formulated and administered systemically. Techniques for formulation and administration may be found in "Remington's Pharmaceutical Sciences", 18th ed., 1990, Mack Publishing Co., Easton, Pa. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. Most preferably, administration is intravenous. For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

In addition, the peptides may be used as a prophylactic measure in previously uninfected individuals after acute exposure to an HIV virus. Examples of such prophylactic use of the peptides may include, but are not limited to, prevention of virus transmission from mother to infant and other settings where the likelihood of HIV transmission exists, such as, for example, accidents in health care settings wherein workers are exposed to HIV-containing blood products. The peptides of the invention in such cases may serve the role of a prophylactic vaccine, wherein the host raises antibodies against the peptides of the invention, which then serve to neutralize HIV viruses by, for example, inhibiting further HIV infection. Administration of the peptides of the invention as a prophylactic vaccine, therefore, would comprise administering to a host a concentration of peptides effective in raising an immune response which is sufficient to neutralize HIV, by, for example, inhibiting HIV ability to infect cells. The exact concentration will depend upon the specific peptide to be administered, but may be determined by using standard techniques for assaying the development of an immune response which are well known to those of ordinary skill in the art. The peptides to be used as vaccines are usually administered intramuscularly.

The peptides may be formulated with a suitable adjuvant in order to enhance the immunological response. Such adjuvants may include, but are not limited to mineral gels such as aluminum hydroxide; surface active substances such as lysolecithin, pluronic polyols, polyanions; other peptides; oil emulsions; and potentially useful human adjuvants such as BCG and Corynebacterium parvum. Many methods may be used to introduce the vaccine formulations described here. These methods include but are not limited to oral, intradermal, intramuscular, intraperitoneal, intravenous, subcutaneous, and intranasal routes.

Alternatively, an effective concentration of polyclonal or monoclonal antibodies raised against the peptides of the invention may be administered to a host so that no uninfected cells become infected by HIV. The exact concentration of such antibodies will vary according to each specific antibody preparation, but may be determined using standard techniques well known to those of ordinary skill in the art. Administration of the antibodies may be accomplished using a variety of techniques, including, but not limited to those described in this section.

Effective dosages of the peptides of the invention to be administered may be determined through procedures well known to those in the art which address such parameters as biological half-life, bioavailability, and toxicity. Given the data presented below in Section 6, DP-178, for example, may prove efficacious in vivo at doses required achieve circulating levels of 10 ng per ml of peptide.

As demonstrated in the Working Example presented below in Section 6, the antiviral activity of the peptides of the invention may show a pronounced type and subtype specificity, i.e., specific peptides may be effective in inhibiting the activity of only specific viruses. This feature of the invention presents many advantages. One such advantage, for example, lies in the field of diagnostics, wherein one can use the antiviral specificity of the peptide of the invention to ascertain the identity of a viral isolate. With respect to HIV, one may easily determine whether a viral isolate consists of an HIV-1 or HIV-2 strain. For example, uninfected CD-4$^+$ cells may be co-infected with an isolate which has been identified as containing HIV the DP-178 (SEQ ID:1) peptide, after which the retroviral activity of cell supernatents may be assayed, using, for example, the techniques described above in Section 5.2. Those isolates whose retroviral activity is completely or nearly completely inhibited contain HIV-1. Those isolates whose viral activity is unchanged or only reduced by a small amount, may be considered to not contain HIV-1. Such an isolate may then be treated with one or more of the other DP-178 peptides of the invention, and subsequently be tested for its viral activity in order to determine the identify of the viral isolate.

6. EXAMPLE: DP-178 (SEQ ID:1) IS A POTENT INHIBITOR OF HIV-1 INFECTION

In this example, DP-178 (SEQ ID:1) is shown to be a potent inhibitor of HIV-1 mediated CD-4$^+$ cell-cell fusion and infection by cell free virus. In the fusion assay, this peptide completely blocks virus induced syncytia formation at concentrations of from 1–10 ng/ml. In the infectivity assay the inhibitory concentration is somewhat higher, blocking infection at 90 ng/ml. It is further shown that DP-178 (SEQ ID:1) shows that the antiviral activity of DP-178 (SEQ ID:1) is highly specific for HIV-1. Additionally, a synthetic peptide, DP-185 (SEQ ID:3), representing a HIV-1-derived DP-178 homolog is also found to block HIV-1-mediated syncytia formation.

6.1 MATERIALS AND METHODS 6.1.1. Peptide Synthesis

Peptides were synthesized using Fast Moc chemistry on an Applied Biosystems Model 431A peptide synthesizer. Amidated peptides were prepared using Rink resin (Advanced Chemtech) while peptides containing free carboxy termini were synthesized on Wang (p-alkoxy-benzyl-alcohol) resin (Bachem). First residues were double coupled to the appropriate resin and subsequent residues were single coupled. Each coupling step was followed by acetic anhydride capping. Peptides were cleaved from the resin by treatment with trifluoracetic acid (TFA) (10 ml), H$_2$O (0.5 ml), thioanisole (0.5 ml), ethanedithiol (0.25 ml), and crystalline phenol (0.75 g). Purification was carried out by reverse phase HPLC. Approximately 50 mg samples of crude peptide were chromatographed on a Waters Delta Pak C18 column (19 mm×30 cm, 15μ spherical) with a linear gradient; H$_2$O/acetonitrile 0.1% TFA. Lyophilized peptides were stored desiccated and peptide solutions were made in water at about 1 mg/ml. Electrospray mass spectrometry yielded the following results: DP-178 (SEQ ID:1):4491.87 (calculated 4491.94); DP-180 (SEQ ID:2):4491.45 (calculated 4491.94); DP-185 (SEQ ID:3):not done (calculated 4546.97).

6.1.2. Virus

The HIV-1$_{LAI}$, virus was obtained from R. Gallo (Popovic, M. et al., 1984, Science 224:497–508) and propagated in CEM cells cultured in RPMI 1640 containing 10% fetal calf serum. Supernatant from the infected CEM cells was passed through a 0.2 μm filter and the infectious titer estimated in a microinfectivity assay using the AA5 cell line to support virus replication. For this purpose, 25 μl of serial diluted virus was added to 75 μl AA5 cells at a concentration of 2×10$^5$/ml in a 96-well microtitre plate. Each virus dilution was tested in triplicate. Cells were cultured for eight days by addition of fresh medium every other day. On day 8 post infection, supernatant samples were tested for virus replication as evidenced by reverse transcriptase activity released to the supernatant. The TCID$_{50}$ was calculated according to the Reed and Muench formula (Reed, L. J. et al., 1938, Am. J. Hyg. 27:493–497). The titer of the HIV-1$_{LAI}$ and HIV-1$_{MN}$ stocks used for these studies, as measured on the AA5 cell line, was approximately 1.4×10$^6$ and 3.8×10$^4$ TCID$_{50}$/ml, respectively.

6.1.3. Cell Fusion Assay

Approximately 7×10$^4$ Molt cells were incubated with 1×10$^4$ CEM cells chronically infected with the HIV-1$_{LAI}$ virus in 96-well plates (one-half area cluster plates; Costar, Cambridge, Mass.) in a final volume of 100 μl culture medium as previously described (Matthews, T. J. et al., 1987, Proc. Natl. Acad. Sci. USA 84: 5424–5428). Peptide inhibitors were added in a volume of 10 μl and the cell mixtures were incubated for 24 hr. at 37° C. At that time, multinucleated giant cells were estimated by microscopic examination at a 40× magnification which allowed visualization of the entire well in a single field.

6.1.4. Cell Free Virus Infection Assay

Synthetic peptides were incubated at 37° C. with either 247 TCID$_{50}$ (for experiment depicted in FIG. 2), or 62 TCID$_{50}$ (for experiment depicted in FIG. 3) units of HIV-1$_{LAI}$ virus or 25 TCID$_{50}$ units of HIV-2$_{NIH2}$ and CEM CD4$^+$ cells at peptide concentrations of 0, 0.04, 0.4, 4.0, and 40 μg/ml for 7 days. The resulting reverse transcriptase (RT) activity in counts per minute was determined using the assay described, below, in Section 6.1.5. See, Reed, L. J. et al., 1938, Am. J. Hyg. 27: 493–497 for an explanation of TCID$_{50}$ calculations.

6.1.5. Reverse Transcriptase Assay

The micro-reverse transcriptase (RT) assay was adapted from Goff et al. (Goff, S. et al., 1981, J. Virol. 38:239–248) and Willey et al. (Willey, R. et al., 1988, J. Virol. 62:139–147). Supertanants from virus/cell cultures are adjusted to 1% Triton-X100. A 10 μl sample of supernatant was added to 50 μl of RT cocktail in a 96-well U-bottom microtitre plate and the samples incubated at 37° C. for 90 min. The RT cocktail contained 75 mM KCl, 2 mM dithiothreitol, 5 mM MgCl$_2$, 5 μg/ml poly A (Pharmacia, cat. No. 27-4110-01) 0.25 units/ml oligo dT (Pharmacia, cat. No. 27-7858-01), 0.05% NP40, 50 mM Tris-HCl, pH 7.8, 0.5 μM non-radioactive dTTP, and 10 μCi/ml $^{32}$P-dTTP (Amersham, cat. No. PB.10167).

After the incubation period, 40 μl of reaction mixture was applied to a Schleicher and Schuell (S+S) NA45 membrane (or DE81 paper) saturated in 2×SSC buffer (0.3M NaCl and 0.003M sodium citrate) held in a S+S Minifold over one sheet of GB003 (S+S) filter paper, with partial vacuum applied. Each well of the minifold was washed four times with 200 μl 2×SSC, under full vacuum. The membrane was removed from the minifold and washed 2 more times in a pyrex dish with an excess of 2×SSC. Finally, the membrane was drained on absorbent paper, placed on Whatman #3 paper, covered with Saran wrap, and exposed to film overnight at −70° C.

6.2 RESULTS

6.2.1. Peptide Inhibition of Infected Cell-Induced Syncytia Formation

The initial screen for antiviral activity assayed peptides' ability to block syncytium formation induced by overnight co-cultivation of uninfected Molt4 cells with chronically HIV-1 infected CEM cells. The results of several such experiments are presented herein. In the first of these experiments, serial DP-178 (SEQ ID:1) peptide concentrations between 10 μg/ml and 12.5 ng/ml were tested for blockade of the cell fusion process. For these experiments, CEM cells chronically infected with either HIV-1$_{LAI}$, HIV-1$_{MN}$, HIV-1$_{RF}$, or HIV-1$_{SF2}$ virus were cocultivated overnight with uninfected Molt 4 cells. The results (FIG. 4) show that DP-178 (SEQ ID:1) afforded complete protection against each of the HIV-1 isolates down to the lowest concentration of DP-178 (SEQ ID:1) used. For HIV$_{LAI}$ inhibition, the lowest concentration tested was 12.5 ng/ml; for all other HIV-1 viruses, the lowest concentration of DP-178 (SEQ ID:1) used in this study was 100 ng/ml. A second peptide, DP-180 (SEQ ID:2), containing the same amino acid residues as DP-178 (SEQ ID:1) but arranged in a random order exhibited no evidence of anti-fusogenic activity even at the high concentration of 40 μg/ml (FIG. 4). These observations indicate that the inhibitory effect of DP-178 (SEQ ID:1) is primary sequence-specific and not related to non-specific peptide/protein interactions. The actual endpoint (i.e., the lowest effective inhibitory concentration) of DP-178 inhibitory action is within the range of 1–10 ng/ml.

The next series of experiments involved the preparation and testing of a DP-178 (SEQ ID:1) homolog for its ability to inhibit HIV-1-induced syncytia formation. As shown in FIG. 1, the sequence of DP-185 (SEQ ID:3) is slightly different from DP-178 (SEQ ID:1) in that its primary sequence is taken from the HIV-1$_{SF2}$ isolate and contains several amino acid differences relative to DP-178 (SEQ ID:1) near the N terminus. As shown in FIG. 4, DP-185 (SEQ ID:3), exhibits inhibitory activity even at 312.5 ng/ml, the lowest concentration tested.

The next series of experiments involved a comparison of DP-178 (SEQ ID:1) HIV-1 and HIV-2 inhibitory activity. As shown in FIG. 5, DP-178 (SEQ ID:1) blocked HIV-1-mediated syncytia formation at peptide concentrations below 1ng/ml. DP-178 (SEQ ID:1) failed, however, to block HIV-2 mediated syncytia formation at concentrations as high as 10 μg/ml. This striking 4 log selectivity of DP-178 (SEQ ID:1) as an inhibitor of HIV-1-mediated cell fusion demonstrates an unexpected HIV-1 specificity in the action of DP-178 (SEQ ID:1). DP-178 (SEQ ID:1) inhibition of HIV-1-mediated cell fusion, but the peptide's inability to inhibit HIV-2 medicated cell fusion in the same cell type at the concentrations tested provides further evidence for the high degree of selectivity associated with the antiviral action of DP-178 (SEQ ID:1).

6.2.2. Peptide Inhibition of Infection by Cell-Free Virus

DP-178 (SEQ ID:1) was next tested for its ability to block CD-4$^+$ CEM cell infection by cell free HIV-1 virus. The results, shown in FIG. 2, are from an experiment in which DP-178 (SEQ ID:1) was assayed for its ability to block infection of CEM cells by an HIV-1$_{LAI}$ isolate. Included in the experiment were three control peptides, DP-116 (SEQ ID:9), DP-125 (SEQ ID:8), and DP-118 (SEQ ID:10). DP-116 (SEQ ID:9) represents a peptide previously shown to be inactive using this assay, and DP-125 (SEQ ID:8; Wild, C. et al., 1992, Proc. Natl. Acad, Sci. USA 89:10,537) and DP-118 (SEQ ID:10) are peptides which have previously been shown to be active in this assay. Each concentration (0, 0.04, 0.4, 4, and 40 μg/ml) of peptide was incubated with 247 $TCID_{50}$ units of $HIV-1_{LAI}$ virus and CEM cells. After 7 days of culture, cell-free supernatant was tested for the presence of RT activity as a measure of successful infection. The results, shown in FIG. 2, demonstrate that DP-178 (SEQ ID:1) inhibited the de novo infection process mediated by the HIV-1 viral isolate at concentrations as low as 90 ng/ml (IC50=90 ng/ml). In contrast, the two positive control peptides, DP-125 (SEQ: ID:8) and DP-118 (SEQ ID:10), had over 60-fold higher IC50 concentrations of approximately 5 μg/ml.

In a separate experiment, the HIV-1 and HIV-2 inhibitory action of DP-178 (SEQ ID:1) was tested with CEM cells and either $HIV-1_{LAI}$ or $HIV-2_{NIHZ}$. 62 $TCID_{50}$ $HIV-1_{LAI}$ or $GCID_{50}$ $HIV-2_{NIHZ}$ were used in these experiments, and were incubated for 7 days. As may be seen in FIG. 3, DP-178 (SEQ ID:1) inhibited HIV-1 infection with an IC50 of about 3.1 ng/ml. In contrast, DP-178 (SEQ ID:1) exhibited a much higher IC50 for $HIV-2_{NIHZ}$, thus making DP-178 (SEQ ID:1) two logs more potent as a HIV-1 inhibitor than a HIV-2 inhibitor. This finding is consistent with the results of the fusion inhibition assays described, above, in Section 6.2.1, and further supports a significant level of selectivity (i.e., for HIV-1 over HIV-2).

7. EXAMPLE: THE HIV-1 INHIBITOR, DP-178 (SEQ ID:1) IS NON-CYTOXIC

In this Example, the 36 amino acid synthetic peptide inhibitor DP-178 (SEQ ID:1) is shown to be non-cytotoxic to cells in culture, even at the highest peptide concentrations (40 μg/ml) tested.

7.1. Materials and Methods

Cell proliferation and toxicity assay: Approximately 3.8× $10^5$ CEM cells for each peptide concentration were incubated for 3 days at 37° C. in T25 flasks. Peptides tested were DP-178 (SEQ ID:1) and DP-116 (SEQ ID:9), as described in FIG. 1. The concentrations of each peptide used were 0, 2.5, 10, and 40 μg/ml. Cell counts were taken at incubation times of 0, 24, 48, and 72 hours.

7.2. Results

Whether the potent HIV-1 inhibitor DP-178 (SEQ ID:1) exhibited any cytotoxic effects was assessed by assaying the peptide's effects on the proliferation and viability of cells in culture. CEM cells were incubated in the presence of varying concentrations of DP-178 (SEQ ID:1), and DP-116 (SEQ ID:9), a peptide previously shown to be ineffective as a HIV inhibitor (Wild, C. et al., 1992, Proc. Natl. Acad. Sci. USA 89:10,537–10,541). Additionally, cells were incubated in the absence of either peptide.

The results of the cytoxicity study demonstrate that DP-178 (SEQ ID:1) exhibits no cytotoxic effects on cells in culture. As can be seen, below, in Table V, even the proliferation and viability characteristics of cells cultured for 3 days in the presence of the highest concentration of DP-178 (SEQ ID:1) tested (40 μg/ml) do not significantly differ from the DP-116 (SEQ ID:9) or the no-peptide controls. The cell proliferation data is also represented in graphic form in FIG. 6. As was demonstrated in the Working Example presented above in Section 6, DP-178 (SEQ ID:1) completely inhibits HIV-1 mediated syncytia formation at peptide concentrations between 1 and 10 ng/ml, and completely inhibits cell-free viral infection at concentrations of at least 90 ng/ml. Thus, this study demonstrates that even at peptide concentrations greater than 3 log higher than the HIV inhibitory dose, DP-178 (SEQ ID:1) exhibits no cytoxic effects.

TABLE V

| Peptide | Peptide Concentration μg/ml | % Viability at time (hours) | | | |
|---|---|---|---|---|---|
| | | 0 | 24 | 48 | 72 |
| DP178 | 40 | 98 | 97 | 95 | 97 |
| (SEQ | 10 | 98 | 97 | 98 | 98 |
| ID:1) | 2.5 | 98 | 93 | 96 | 96 |
| DP116 | 40 | 98 | 95 | 98 | 97 |
| (SEQ | 10 | 98 | 95 | 93 | 98 |
| ID:9) | 2.5 | 98 | 96 | 98 | 99 |
| No Peptide | 0 | 98 | 97 | 99 | 98 |

It is apparent that many modifications of this invention as set forth here may be made without departing from the spirit and scope thereof. The specific embodiments described hereinabove are given by way of example only and not by way of limitation. The invention, therefore, is limited only by the terms of the appended claims.

What is claimed is:

1. A peptide having the formula

X-YTSLIHSLIEESQNQQEKNEQELLELDKWASLWNWF-Z (SEQ ID NO:1)

in which amino acid residues are presented by the single-letter code wherein:

X is an amino group, an acetyl group, a 9-fluorenylmethoxy-carbonyl group, or a hydrophobic group; and Z is a carboxyl group, an amido group, or a hydrophobic group.

2. A peptide having the formula

X-YTSLIHSLIEESQNQQEKNEQELLELDKWASLWNWF-Z (SEQ ID NO: 1)

in which amino acid residues are presented by the single-letter code wherein:

X is an acetyl group; and

Z is an amido group.

3. A pharmaceutical composition comprising an effective amount of the peptide of claim 2 and a pharmaceutically acceptable carrier or excipient.

* * * * *

UNITED STATES PATENT AND TRADEMARK OFFICE
CERTIFICATE OF CORRECTION

PATENT NO.    : 6,133,418
DATED         : October 17, 2000
INVENTOR(S)   : Bolognesi et al.

It is certified that error appears in the above-identified patent and that said Letters Patent is hereby corrected as shown below:

Title page,
Item [56], after References Cited, please insert the heading "U.S. PATENT DOCUMENTS"
Under the newly inserted heading U.S. PATENT DOCUMENTS, please insert the following patent citations:

| Patent No. | Date | Inventor |
|---|---|---|
| 5,444,044 | 8/95 | Jiang et al. |
| 5,141,867 | 8/92 | Ivanoff et al. |
| 5,116,725 | 5/92 | Vaughan et al. |
| 5,075,211 | 12/91 | Cosand et al. |
| 4,880,779 | 11/89 | Gallaher |
| 4,761,470 | 8/88 | Emini et al. |
| 4,707,358 | 11/87 | Kleff et al. |
| 4,659,669 | 4/87 | Kleid et al. |
| 4,638,047 | 1/87 | Szelke et al. |

Under the heading FOREIGN PATENT DOCUMENTS, please insert the following after the two cited references listed:

| Document No. | Date | Country |
|---|---|---|
| WO 92/22654 | 12/92 | PCT |
| 2,677,346 | 12/92 | France |
| WO 92/00997 | 1/92 | PCT |
| WO 90/07119 | 6/90 | PCT |
| 0 371 817 | 6/90 | EPO |
| 0 362 927 | 4/90 | EPO |
| 0 323 424 | 7/89 | EPO |
| 27573/88 | 6/89 | Australia |
| WO 89/02935 | 4/89 | PCT |
| 0 323 157 | 12/88 | EPO |
| WO 87/06005 | 10/87 | PCT |

Please insert the heading "OTHER PUBLICATIONS", and insert the following list of publications:

Abel and Maniatis, 1989, "Action of Leucine Zippers", Nature 341:24-25
"HIV Protease Inhibitors", 1990, ASM News 56:368
Barin et al., 1985, "Virus Envelope Protein of HTLV-III Represents Major Target Antigen for Antibodies in AIDS Patients", Science 228:1094-1096
Barré-Sinoussi et al., 1983, Isolation of a T-Lymphotropic Retrovirus from a Patient at Risk for Acquired Immune Deficiency Syndrome (AIDS)", Science 220:868-870
Baum et al., 1997, "Also..", Immunol. Today 18:252-253
Benet et al., 1990, "Pharmacokinetics: the Dynamics of Drug Absorption, Distribution and Elimination", in: The Pharmacological Basis of Therapeutics, 8th Edition, Goodman et al., eds., Pergammon Press, NY, pp. 3-32
Bousse et al., 1995, "A Single Amino Acid Change Enhances the Fusion Promotion Activity of Human Parainfluenza Virus Type1 Hemagglutinin-Neuraminidase Glycoprotein", Virol. 209:654-657
Bousse et al., 1994, "Regions on the Hemagglutinin-Neuraminidase Proteins of Human Parainfluenza Virus Type 1 and Sendai Virus Important for Membrane Fusion", Virol. 204:506-514
Buckland et al., 1992, "A Leucine Zipper Structure Present in the Measles Virus Fusion Protein is not Required for Its Tetramerization but Is Essential for Fusion", J. Gen. Virol. 73:1703-1707
Carr and Kim, 1993, "A Spring-Loaded Mechanism for the Conformational Change of Influenza Hemagglutinin", Cell 73:823-832
Chakrabarti et al. 1987, "Sequence of Simian Immunodeficiency Virus from Macaque and Its Relationship to Other Human and Simian Retroviruses", Nature 328:543-547

UNITED STATES PATENT AND TRADEMARK OFFICE
CERTIFICATE OF CORRECTION

PATENT NO.    : 6,133,418
DATED         : October 17, 2000
INVENTOR(S)   : Bolognesi et al.

It is certified that error appears in the above-identified patent and that said Letters Patent is hereby corrected as shown below:

OTHER PUBLICATIONS, (cont'd),

Chambers et al., 1990, "Heptad Repeat Sequences are Located Adjacent to Hydrophobic Regions in Several Types of Virus Fusion Glycoproteins", J. Gen. Virol. 71:3075-3080
Chen, 1994, "Functional Role of the Zipper Motif Region of Human Immunodeficiency Virus Type I Transmembrane Protein gp41", J. Virol. 68:2002-2010
Clavel et al., 1986, "Isolation of a New Human Retrovirus from West African Patients with AIDS", Science 233:343-346
Collins et al., 1984, "Nucleotide Sequence of the Gene Encoding the Fusion (F) Glycoprotein of Human Respiratory Syncytial Virus", Proc. Natl. Acad. Sci. USA 81:7683-7687
Crowl et al., 1985, "HTLV-III env Gene Products Synthesized in E. coli are Recognized by Antibodies Present in the Sera of AIDS Patients", Cell 41:979-986
Daar et al., 1990, "High Concentrations of Recombinant Soluble CD40 are Required to Neutralize Primary Human Immunodeficiency Virus Type 1 Isolates", Proc. Natl. Acad. Sci USA 87:6574-6579
Dalgleish et al., 1984, "The CD4 (T4) Antigen is an Essential Component of the Receptor for the AIDS Retrovirus", Nature 312:763-767
Davey et al., 1993, "Plasma Viremia as a Sensitive Indicator of the Antiretroviral Activity of L-697,661", Proc. Natl. Acad. Sci. USA 90:5608-5612
Delwart et al., 1990, "Retroviral Envelope Glycoproteins Contain a "Leucine Zipper"-Like Repeat", AIDS Res. Human Retroviruses 6:703-706
Dubay et al., 1992, "Mutations in the Leucine Zipper of the Human Immunodeficiency Virus Type I Transmembrane Glycoprotein Affect Fusion and Infectivity", J. Virol. 66:4748-4756
Dubay et al., 1991, "Structure-Function Analysis of the HIV Glycoprotein", Adv. Exp. Med. Biol. 303:39-46
Erickson et al., 1990, "Design, Activity and 2.8 Å Crystal Structure of a $C_2$ Symmetric Inhibitor Complexed to HIV-1 Protease", Science 249:527-533
Franchini et al., 1987, "Sequence of Simian Immunodeficiency Virus and Its Relationship to the Human Immunodeficiency Viruses", Nature 328:539-543
Gait et al., 1995, "Progress in Anti-HIV Structure-Based Drug Design", TIBTECH 13:430-438
Gallaher, 1987, "Detection of a Fusion Peptide Sequence in the Transmembrane Protein of Human Immunodeficiency Virus", Cell 50:327-328
Gallaher et al., 1989, "A General Model for the Transmembrane Proteins of HIV and Other Retroviruses", AIDS Res. and Human Retroviruses 5:431-440

UNITED STATES PATENT AND TRADEMARK OFFICE
CERTIFICATE OF CORRECTION

PATENT NO.    : 6,133,418
DATED         : October 17, 2000
INVENTOR(S)   : Bolognesi et al.

It is certified that error appears in the above-identified patent and that said Letters Patent is hereby corrected as shown below:

OTHER PUBLICATIONS, (cont'd),

Gallaher et al., 1992, "Are Fusion Peptides Really "Sided" Insertional Helices?", Cell 70:531-532
Gallaher et al., 1992, "Membrane Interactions of Human Immunodeficiency Virus: Attachment, Fusion, and Cytopathology", in: Advances in Membrane Fluidity, Wiley-Liss, Inc., pp. 113-142
Gallo et al., 1984, "Frequent Detection and Isolation of Cytopathic Retroviruses (HTLV-III) from Patients with AIDS and at Risk for AIDS", Science 224:500-503
Geysen et al., 1988, "Cognitive Features of Continuous Antigenic Determinants", J. Molec. Recognition 1:33-41
Guyader et al., 1987, "Genome Organization and Transactivation of the Human Immunodeficiency Virus Type 2", Nature 326:662-669
Hall, 1994, "Prospects for a Respiratory Syncytial Virus Vaccine", Science 265:1393-1394
Hammarskjöld and Rekosh, 1989, "The Molecular Biology of the Human Immunodeficiency Virus", Biochem. Biophys. Acta 989:269-280
Hammer et al., 1994, "Issues in Combination Antiretroviral Therapy: A Review", J. Acq. Imm. Def. Syn. 7(suppl. 2):S24-S37
Jiang et al. 1993, "Inhibition of HIV-1 Infection by a Fusion Domain Binding Peptide from the HIV-1 Envelope Glycoprotein gp41", Biochem. Biophys. Res. Comm. 195:533-538
Kahn et al., 1990, "The Safety and Pharmacokinetics of Recombinant Soluble CD4 (rCD4) in Subjects with the Acquired Immunodeficiency Syndrome (AIDS) and AIDS-Related Complex", Ann. Int. Med. 112:254-261
Kingsbury, 1990, "Paramyxoviridae and their Replication", in: Virology, 2nd Ed., Fields et al., eds., Raven Press, NY, pp. 951
Klatzmann et al., 1984, "T-Lymphocyte T4 Molecule Behaves as the Receptor for Human Retrovirus LAV", Nature 312:767-768
Kucera et al., 1990, "Novel Membrane-Interactive Ether Lipid Analogs that Inhibit Infectious HIV-1 Production and Induce Defective Virus Formation", AIDS Res. Hum. Retroviruses 6:491-501
Lam et al., 1991, "A New Type of Synthetic Peptide Library for Identifying Ligand-Binding Activity", Nature 354:82-84
Larder et al., 1989, "HIV with Reduced Sensitivity to Zidovudine (AZT) Isolated During Prolonged Therapy", Science 243:1731-1734
Lazinski and Taylor, 1993, "Relating Structure to Function in the Hepatitis Delta Virus Antigen", J. Virol. 67:2672-2680

UNITED STATES PATENT AND TRADEMARK OFFICE
CERTIFICATE OF CORRECTION

PATENT NO. : 6,133,418
DATED : October 17, 2000
INVENTOR(S) : Bolognesi et al.

It is certified that error appears in the above-identified patent and that said Letters Patent is hereby corrected as shown below:

OTHER PUBLICATIONS, (cont'd),

Leff, 1994, "Finally, a True Primate Model for AIDS", Bioworld Today, Vol. 5, no. 210, pp. 1,5
Lupas et al., 1991, "Predicting Coiled Coils from Protein Sequences", Science 252:1162-1165
Maddon et al., 1986, "The T4 Gene Encodes the AIDS Virus Receptor and is Expressed in the Immune System and the Brain", Cell 47:333-348
Malim et al., 1988, "Immunodeficiency Virus rev trans-Activator Modulates the Expression of the Viral Regulatory Genes", Nature 335:181-183
McDougal et al., 1986, "Binding of HTLV-III/LAV to T4+ T Cells by a Complex of the 110k Viral Protein and the T4 Molecule", Science 231:382-385
Mitsuya et al., 1990, "Molecular Targets for AIDS Therapy", Science 249:1533-1544
Mitsuya et al., 1991, "Targeted Therapy of Human Immunodeficiency Virus-Related Disease", FASEB J. 5:2369-2381
Neurath et al., 1992, "Synthetic Peptides and Anti-Peptide Antibodies as Probes to Study Interdomain Interactions Involved in Virus Assembly: the Envelope of the Human Immunodeficiency Virus (HIV-1)", Virology 188:1-13
Okamoto et al., 1988, "Typing Hepatitis B Virus by Homology in Nucleotide Sequence: Comparison of Surface Antigen Subtypes", J. Gen. Virol. 69:2575-2583
O'Shea et al., 1989, "Evidence that the Leucine Zipper is a Coiled Coil", Science 243:538-542
Pert et al., 1986, "Octapeptides Deduced from the Neuropeptide Receptor-Like Pattern of Antigen T4 in Brain Potently Inhibit Human Immunodeficiency Virus Receptor Binding and T-Cell Infectivity", Proc. Natl. Acad. Sci. USA 83:9254-9258
Qureshi et al., 1990, "Characterization of a Putative Cellular Receptor for HIV-1 Transmembrane Glycoprotein Using Synthetic Peptides", AIDS 4:553-558
Richardson et al., 1980, "Specific Inhibition of Paramyxovirus and Myxovirus Replication by Oligopeptides with Amino Acid Sequences Similar to Those at the N-Termini of the $F_1$ or $HA_2$ Viral Polypeptides", Virol. 105:205-222
Richardson et al., 1986, "The Nucleotide Sequence of the mRNA Encoding the Fusion Protein of Measles Virus (Edmonston Strain): A Comparison of Fusion Proteins from Several Different Paramyxoviruses", Virol. 155:508-523
Richman et al., 1994, "Nevirapine Resistance Mutations of Human Immunodeficiency Virus Type 1 Selected During Therapy", J. Virol. 68:1660-1666

UNITED STATES PATENT AND TRADEMARK OFFICE
CERTIFICATE OF CORRECTION

PATENT NO. : 6,133,418
DATED : October 17, 2000
INVENTOR(S) : Bolognesi et al.

It is certified that error appears in the above-identified patent and that said Letters Patent is hereby corrected as shown below:

OTHER PUBLICATIONS, (cont'd),

Roudier, 1997, "Response to Wildner et al. and Burns et al.", Immunol. Today 18:263
Ruegg et al., 1989, "Inhibition of Lymphoproliferation by a Synthetic Peptide with Sequence Identity to gp41 of Human Immunodeficiency Virus Type 1", J. Virol. 63:3257-3260
Saag et al., 1994, "Pathogenicity and Diversity of HIV and Implications for Clinical Management: A Review", J. Acq. Imm. Def. Syn. 7(suppl. 2):S2-S11
Schooley et al., 1990, "Recombinant Soluble CD4 Therapy in Patients with the Acquired Immune Deficiency Syndrome (AIDS) and AIDS-Related Complex. A Phase I-II Escalating Dosage Trial", Ann. Int. Med. 112:247-253
Smith et al., 1987, "Blocking of HIV-1 Infectivity by a Soluble, Secreted Form of the CD4 Antigen", Science 238:1704-1707
Songyang et al., 1993, "SH2 Domains Recognize Specific Phosphopeptide Sequences", Cell 72:767-778
Spalding, 1992, "In Hot Pursuit of an HIV Vaccine", Bio/Technology 10:24-29
Srinivas, 1992, "Inhibitors of Human Immunodeficiency Virus-Induced Membrane Fusion", In: Membrane Interactions of HIV: Implications for Pathogenesis and Therapy in AIDS, Aloia and Curtain, eds., Wiley-Liss, NY, pp. 187-202
Staden, 1994, "Searching for Motifs in Protein Sequences", in: Methods in Molecular Biology, Vol. 25: Computer Analysis of Sequence Data, Part II, Griffin et al., eds., Humana Press, Totowa, NJ, pp. 131-139
Staden, 1994, "Using Patterns to Analyze Protein Sequences", in: Methods in Molecular Biology, Vol. 25: Computer Analysis of Sequence Data, Part II, Griffin et al., eds., Humana Press, Totowa, NJ, pp. 141-154
Staden, 1990, "Searching for Patterns in Protein and Nucleic Acid Sequences", Meth. Enzymol. 183:193-211
Suzuki et al., 1995, "Viral Interleukin 10 (IL-10), the Human Herpes Virus 4 Cellular IL-10 Homologue, Induces Local Anergy to Allogeneic and Syngeneic Tumors", J. Exp. Med. 182:477-486
Teich et al., 1984, "Pathogenesis of Lentivirus", in: RNA Tumor Viruses, Weiss et al., eds., CSH Press, pp. 949-956
Toms, 1995, "Respiratory Syncytial Virus - How Soon Will We Have a Vaccine?", Arch. Dis. Child. 72:1-3
Tyler et al., 1990, "Identification of Sites within gp41 that Serve as Targets for Antibody-Dependent Cellular Cytotoxicity by Using Human Monoclonal Antibodies", J. Immunol. 145:3276-3282

UNITED STATES PATENT AND TRADEMARK OFFICE
CERTIFICATE OF CORRECTION

PATENT NO. : 6,133,418
DATED : October 17, 2000
INVENTOR(S) : Bolognesi et al.

It is certified that error appears in the above-identified patent and that said Letters Patent is hereby corrected as shown below:

OTHER PUBLICATIONS, (cont'd),

Varsanyi et al., 1985, "Isolation and Characterization of the Measles Virus $F_1$ Polypeptide: Comparison with Other Paramyxovirus Fusion Proteins", Virol. 147:110-117
Wang et al., 1993, "Ion Channel Activity of Influenza A Virus $M_2$ Protein: Characterization of the Amantadine Block", J. Virol. 67:5585-6594
White, 1992, "Membrane Fusion", Science 258:917-924
Wild et al., 1994, "Propensity for a Leucine Zipper-Like Domain of Human Immunodeficiency Virus Type 1 gp41 to Form Oligomers Correlates with a Role in Virus-Induced Fusion rather than Assembly of the Glycoprotein Complex", Proc. Natl. Acad. Sci. USA 91:12676-12680
Wild et al., 1994, "Peptides Corresponding to a Predictive α-Helical Domain of Human Immunodeficiency Virus Type 1 gp41 Are Potent Inhibitors of Virus Infection", Proc. Natl. Acad. Sci USA 91:9770-9774
Wild et al., 1993, "A Synthetic Peptide from HIV-1 gp41 Is a Potent Inhibitor of Virus-Mediated Cell-Cell Fusion", AIDS Res. and Human Retroviruses 9:1051-1053
Wild et al., 1992, "A Synthetic Peptide Inhibitor of Human Immunodeficiency Virus Replication: Correlation between Solution Structure and Viral Inhibition", Proc. Natl. Acad. Sci USA 89:10537-10541
Wildner and Thurau, 1997, "Database Screening for Molecular Mimicry", Immunol. Today 18:252
Xu et al., 1991, "Epitope Mapping of Two Immunodominant Domains of gp41, the Transmembrane Protein of Human Immunodeficiency Virus Type 1, Using Ten Human Monoclonal Antibodies", J. Virol. 65:4832-4838
Yarchoan et al., 1989, "Phase I Study of the Administration of Recombinant Soluble CD4 (rCD4) by Continuous Infusion to Patients with AIDS or ARC", Proc. Vth Int. Conf. on AIDS, p. 564, MCP 137
Yarchoan and Broder, 1992, "Correlations between the *in vitro* and *In vivo* Activity of Anti-HIV Agents: Implications for Future Drug Development", J. Enzyme Inhib. 6:99-111

Signed and Sealed this

Third Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,133,418
DATED : October 17, 2000
INVENTOR(S) : Bolognesi et al.

It is certified that error appears in the above-identified patent and that said Letters Patent is hereby corrected as shown below:

<u>Title page,</u>
Item [56], References Cited, U.S. PATENT DOCUMENTS, please insert the following:

| | | |
|---|---|---|
| 5,444,044 | 8/95 | Jiang et al. |
| 5,141,867 | 8/92 | Ivanoff et al. |
| 5,116,725 | 5/92 | Vaughan et al. |
| 5,075,211 | 12/91 | Cosand et al. |
| 4,880,779 | 11/89 | Gallaher |
| 4,761,470 | 8/88 | Emini et al. |
| 4,707,358 | 11/87 | Kleff et al. |
| 4,659,669 | 4/87 | Kleid et al. |
| 4,638,047 | 1/87 | Szelke et al. |

FOREIGN PATENT DOCUMENTS, please insert the following:

| | | |
|---|---|---|
| WO 92/22654 | 12/92 | PCT |
| 2,677,346 | 12/92 | France |
| WO 92/00997 | 1/92 | PCT |
| WO 90/07119 | 6/90 | PCT |
| 0 371 817 | 6/90 | EPO |
| 0 362 927 | 4/90 | EPO |
| 0 323 424 | 7/89 | EPO |
| 27573/88 | 6/89 | Australia |
| WO 89/02935 | 4/89 | PCT |
| 0 323 157 | 12/88 | EPO |
| WO 87/06005 | 10/87 | PCT |

UNITED STATES PATENT AND TRADEMARK OFFICE
CERTIFICATE OF CORRECTION

PATENT NO.    : 6,133,418
DATED         : October 17, 2000
INVENTOR(S)   : Bolognesi et al.

It is certified that error appears in the above-identified patent and that said Letters Patent is hereby corrected as shown below:

Title page (cont'd),
OTHER PUBLICATIONS, please insert the following:

Abel and Maniatis, 1989, "Action of Leucine Zippers", Nature 341:24-25
"HIV Protease Inhibitors", 1990, ASM News 56:368
Barin et al., 1985, "Virus Envelope Protein of HTLV-III Represents Major Target Antigen for Antibodies in AIDS Patients", Science 228:1094-1096
Barré-Sinoussi et al., 1983, Isolation of a T-Lymphotropic Retrovirus from a Patient at Risk for Acquired Immune Deficiency Syndrome (AIDS)", Science 220:868-870
Baum et al., 1997, "Also..", Immunol. Today 18:252-253
Benet et al., 1990, "Pharmacokinetics: the Dynamics of Drug Absorption, Distribution and Elimination", in: The Pharmacological Basis of Therapeutics, 8th Edition, Goodman et al., eds., Pergammon Press, NY, pp. 3-32
Bousse et al., 1995, "A Single Amino Acid Change Enhances the Fusion Promotion Activity of Human Parainfluenza Virus Type1 Hemagglutinin-Neuraminidase Glycoprotein", Virol. 209:654-657
Bousse et al., 1994, "Regions on the Hemagglutinin-Neuraminidase Proteins of Human Parainfluenza Virus Type 1 and Sendai Virus Important for Membrane Fusion", Virol. 204:506-514
Buckland et al., 1992, "A Leucine Zipper Structure Present in the Measles Virus Fusion Protein is not Required for its Tetramerization but is Essential for Fusion", J. Gen. Virol. 73:1703-1707
Carr and Kim, 1993, "A Spring-Loaded Mechanism for the Conformational Change of Influenza Hemagglutinin", Cell 73:823-832
Chakrabarti et al. 1987, "Sequence of Simian Immunodeficiency Virus from Macaque and Its Relationship to Other Human and Simian Retroviruses", Nature 328:543-547

Chambers et al., 1990, "Heptad Repeat Sequences are Located Adjacent to Hydrophobic Regions in Several Types of Virus Fusion Glycoproteins", J. Gen. Virol. 71:3075-3080
Chen, 1994, "Functional Role of the Zipper Motif Region of Human Immunodeficiency Virus Type I Transmembrane Protein gp41", J. Virol. 68:2002-2010
Clavel et al., 1986, "Isolation of a New Human Retrovirus from West African Patients with AIDS", Science 233:343-346
Collins et al., 1984, "Nucleotide Sequence of the Gene Encoding the Fusion (F) Glycoprotein of Human Respiratory Syncytial Virus", Proc. Natl. Acad. Sci. USA 81:7683-7687
Crowl et al., 1985, "HTLV-III env Gene Products Synthesized in E. coli are Recognized by Antibodies Present in the Sera of AIDS Patients", Cell 41:979-986

UNITED STATES PATENT AND TRADEMARK OFFICE
CERTIFICATE OF CORRECTION

PATENT NO. : 6,133,418
DATED : October 17, 2000
INVENTOR(S) : Bolognesi et al.

It is certified that error appears in the above-identified patent and that said Letters Patent is hereby corrected as shown below:

Title page (cont'd),
OTHER PUBLICATIONS, please insert the following:

Daar et al., 1990, "High Concentrations of Recombinant Soluble CD40 are Required to Neutralize Primary Human Immunodeficiency Virus Type 1 Isolates", Proc. Natl. Acad. Sci USA 87:6574-6579
Dalgleish et al., 1984, "The CD4 (T4) Antigen is an Essential Component of the Receptor for the AIDS Retrovirus", Nature 312:763-767
Davey et al., 1993, "Plasma Viremia as a Sensitive Indicator of the Antiretroviral Activity of L-697,661", Proc. Natl. Acad. Sci. USA 90:5608-5612
Delwart et al., 1990, "Retroviral Envelope Glycoproteins Contain a "Leucine Zipper"-Like Repeat", AIDS Res. Human Retroviruses 6:703-706
Dubay et al., 1992, "Mutations in the Leucine Zipper of the Human Immunodeficiency Virus Type I Transmembrane Glycoprotein Affect Fusion and Infectivity", J. Virol. 66:4748-4756
Dubay et al., 1991, "Structure-Function Analysis of the HIV Glycoprotein", Adv. Exp. Med. Biol. 303:39-46
Erickson et al., 1990, "Design, Activity and 2.8 Å Crystal Structure of a $C_2$ Symmetric Inhibitor Complexed to HIV-1 Protease", Science 249:527-533
Franchini et al., 1987, "Sequence of Simian Immunodeficiency Virus and Its Relationship to the Human Immunodeficiency Viruses", Nature 328:539-543
Gait et al., 1995, "Progress in Anti-HIV Structure-Based Drug Design", TIBTECH 13:430-438
Gallaher, 1987, "Detection of a Fusion Peptide Sequence in the Transmembrane Protein of Human Immunodeficiency Virus", Cell 50:327-328
Gallaher et al., 1989, "A General Model for the Transmembrane Proteins of HIV and Other Retroviruses", AIDS Res. and Human Retroviruses 5:431-440

Gallaher et al., 1992, "Are Fusion Peptides Really "Sided" Insertional Helices?", Cell 70:531-532
Gallaher et al., 1992, "Membrane Interactions of Human Immunodeficiency Virus: Attachment, Fusion, and Cytopathology", In: Advances in Membrane Fluidity, Wiley-Liss, Inc., pp. 113-142
Gallo et al., 1984, "Frequent Detection and Isolation of Cytopathic Retroviruses (HTLV-III) from Patients with AIDS and at Risk for AIDS", Science 224:500-503
Geysen et al., 1988, "Cognitive Features of Continuous Antigenic Determinants", J. Molec. Recognition 1:33-41
Guyader et al., 1987, "Genome Organization and Transactivation of the Human Immunodeficiency Virus Type 2", Nature 326:662-669
Hall, 1994, "Prospects for a Respiratory Syncytial Virus Vaccine", Science 265:1393-1394
Hammarskjöld and Rekosh, 1989, "The Molecular Biology of the Human Immunodeficiency Virus", Biochem. Biophys. Acta 989:269-280
Hammer et al., 1994, "Issues in Combination Antiretroviral Therapy: A Review", J. Acq. Imm. Def. Syn. 7(suppl. 2):S24-S37

UNITED STATES PATENT AND TRADEMARK OFFICE
CERTIFICATE OF CORRECTION

PATENT NO. : 6,133,418
DATED : October 17, 2000
INVENTOR(S) : Bolognesi et al.

It is certified that error appears in the above-identified patent and that said Letters Patent is hereby corrected as shown below:

Title page (cont'd),
OTHER PUBLICATIONS, please insert the following:

Jiang et al. 1993, "Inhibition of HIV-1 Infection by a Fusion Domain Binding Peptide from the HIV-1 Envelope Glycoprotein gp41", Biochem. Biophys. Res. Comm. 195:533-538
Kahn et al., 1990, "The Safety and Pharmacokinetics of Recombinant Soluble CD4 (rCD4) in Subjects with the Acquired Immunodeficiency Syndrome (AIDS) and AIDS-Related Complex", Ann. Int. Med. 112:254-261
Kingsbury, 1990, "Paramyxoviridae and their Replication", in: Virology, 2$^{nd}$ Ed., Fields et al., eds., Raven Press, NY, pp. 951
Klatzmann et al., 1984, "T-Lymphocyte T4 Molecule Behaves as the Receptor for Human Retrovirus LAV", Nature 312:767-768
Kucera et al., 1990, "Novel Membrane-Interactive Ether Lipid Analogs that Inhibit Infectious HIV-1 Production and Induce Defective Virus Formation", AIDS Res. Hum. Retroviruses 6:491-501
Lam et al., 1991, "A New Type of Synthetic Peptide Library for Identifying Ligand-Binding Activity", Nature 354:82-84
Larder et al., 1989, "HIV with Reduced Sensitivity to Zidovudine (AZT) Isolated During Prolonged Therapy", Science 243:1731-1734
Lazinski and Taylor, 1993, "Relating Structure to Function in the Hepatitis Delta Virus Antigen", J. Virol. 67:2672-2680

Leff, 1994, "Finally, a True Primate Model for AIDS", Bioworld Today, Vol. 5, no. 210, pp. 1,5
Lupas et al., 1991, "Predicting Coiled Coils from Protein Sequences", Science 252:1162-1165
Maddon et al., 1986, "The T4 Gene Encodes the AIDS Virus Receptor and is Expressed in the Immune System and the Brain", Cell 47:333-348
Malim et al., 1988, "Immunodeficiency Virus rev trans-Activator Modulates the Expression of the Viral Regulatory Genes", Nature 335:181-183
McDougal et al., 1986, "Binding of HTLV-III/LAV to T4$^+$ T Cells by a Complex of the 110k Viral Protein and the T4 Molecule", Science 231:382-385
Mitsuya et al., 1990, "Molecular Targets for AIDS Therapy", Science 249:1533-1544
Mitsuya et al., 1991, "Targeted Therapy of Human Immunodeficiency Virus-Related Disease", FASEB J. 5:2369-2381
Neurath et al., 1992, "Synthetic Peptides and Anti-Peptide Antibodies as Probes to Study Interdomain Interactions Involved in Virus Assembly: the Envelope of the Human Immunodeficiency Virus (HIV-1)", Virology 188:1-13
Okamoto et al., 1988, "Typing Hepatitis B Virus by Homology in Nucleotide Sequence: Comparison of Surface Antigen Subtypes", J. Gen. Virol. 69:2575-2583
O'Shea et al., 1989, "Evidence that the Leucine Zipper is a Coiled Coil", Science 243:538-542

UNITED STATES PATENT AND TRADEMARK OFFICE
CERTIFICATE OF CORRECTION

PATENT NO. : 6,133,418
DATED : October 17, 2000
INVENTOR(S) : Bolognesi et al.

It is certified that error appears in the above-identified patent and that said Letters Patent is hereby corrected as shown below:

Title page (cont'd),
OTHER PUBLICATIONS, please insert the following:

Pert et al., 1986, "Octapeptides Deduced from the Neuropeptide Receptor-Like Pattern of Antigen T4 in Brain Potently Inhibit Human Immunodeficiency Virus Receptor Binding and T-Cell Infectivity", Proc. Natl. Acad. Sci. USA 83:9254-9258

Qureshi et al., 1990, "Characterization of a Putative Cellular Receptor for HIV-1 Transmembrane Glycoprotein Using Synthetic Peptides", AIDS 4:553-558

Richardson et al., 1980, "Specific Inhibition of Paramyxovirus and Myxovirus Replication by Oligopeptides with Amino Acid Sequences Similar to Those at the N-Termini of the $F_1$ or $HA_2$ Viral Polypeptides", Virol. 105:205-222

Richardson et al., 1986, "The Nucleotide Sequence of the mRNA Encoding the Fusion Protein of Measles Virus (Edmonston Strain): A Comparison of Fusion Proteins from Several Different Paramyxoviruses", Virol. 155:508-523

Richman et al., 1994, "Nevirapine Resistance Mutations of Human Immunodeficiency Virus Type 1 Selected During Therapy", J. Virol. 68:1660-1666

Roudier, 1997, "Response to Wildner et al. and Burns et al.", Immunol. Today 18:253

Ruegg et al., 1989, "Inhibition of Lymphoproliferation by a Synthetic Peptide with Sequence Identity to gp41 of Human Immunodeficiency Virus Type 1", J. Virol. 63:3257-3260

Saag et al., 1994, "Pathogenicity and Diversity of HIV and Implications for Clinical Management: A Review", J. Acq. Imm. Def. Syn. 7(suppl. 2):S2-S11

Schooley et al., 1990, "Recombinant Soluble CD4 Therapy in Patients with the Acquired Immune Deficiency Syndrome (AIDS) and AIDS-Related Complex. A Phase I-II Escalating Dosage Trial", Ann. Int. Med. 112:247-253

Smith et al., 1987, "Blocking of HIV-1 Infectivity by a Soluble, Secreted Form of the CD4 Antigen", Science 238:1704-1707

Songyang et al., 1993, "SH2 Domains Recognize Specific Phosphopeptide Sequences", Cell 72:767-778

Spalding, 1992, "In Hot Pursuit of an HIV Vaccine", Bio/Technology 10:24-29

Srinivas, 1992, "Inhibitors of Human Immunodeficiency Virus-Induced Membrane Fusion", in: Membrane Interactions of HIV: Implications for Pathogenesis and Therapy in AIDS, Aloia and Curtain, eds., Wiley-Liss, NY, pp. 187-202

Staden, 1994, "Searching for Motifs in Protein Sequences", in: Methods in Molecular Biology, Vol. 25: Computer Analysis of Sequence Data, Part II, Griffin et al., eds., Humana Press, Totowa, NJ, pp. 131-139

Staden, 1994, "Using Patterns to Analyze Protein Sequences", in: Methods in Molecular Biology, Vol. 25: Computer Analysis of Sequence Data, Part II, Griffin et al., eds., Humana Press, Totowa, NJ, pp. 141-154

Staden, 1990, "Searching for Patterns in Protein and Nucleic Acid Sequences", Meth. Enzymol. 183:193-211

UNITED STATES PATENT AND TRADEMARK OFFICE
CERTIFICATE OF CORRECTION

PATENT NO.   : 6,133,418
DATED        : October 17, 2000
INVENTOR(S)  : Bolognesi et al.

It is certified that error appears in the above-identified patent and that said Letters Patent is hereby corrected as shown below:

Title page (cont'd),
OTHER PUBLICATIONS, please insert the following:

Suzuki et al., 1995, "Viral Interleukin 10 (IL-10), the Human Herpes Virus 4 Cellular IL-10 Homologue, Induces Local Anergy to Allogeneic and Syngeneic Tumors", J. Exp. Med. 182:477-486
Teich et al., 1984, "Pathogenesis of Lentivirus", in: RNA Tumor Viruses, Weiss et al., eds., CSH Press, pp. 949-956
Toms, 1995, "Respiratory Syncytial Virus - How Soon Will We Have a Vaccine?", Arch. Dis. Child. 72:1-3
Tyler et al., 1990, "Identification of Sites within gp41 that Serve as Targets for Antibody-Dependent Cellular Cytotoxicity by Using Human Monoclonal Antibodies", J. Immunol. 145:3276-3282

Varsanyi et al., 1985, "Isolation and Characterization of the Measles Virus $F_1$ Polypeptide: Comparison with Other Paramyxovirus Fusion Proteins", Virol. 147:110-117
Wang et al., 1993, "Ion Channel Activity of Influenza A Virus $M_2$ Protein: Characterization of the Amantadine Block", J. Virol. 67:5585-5594
White, 1992, "Membrane Fusion", Science 258:917-924
Wild et al., 1994, "Propensity for a Leucine Zipper-Like Domain of Human Immunodeficiency Virus Type 1 gp41 to Form Oligomers Correlates with a Role in Virus-Induced Fusion rather than Assembly of the Glycoprotein Complex", Proc. Natl. Acad. Sci. USA 91:12676-12680
Wild et al., 1994, "Peptides Corresponding to a Predictive α-Helical Domain of Human Immunodeficiency Virus Type 1 gp41 Are Potent Inhibitors of Virus Infection", Proc. Natl. Acad. Sci USA 91:9770-9774
Wild et al., 1993, "A Synthetic Peptide from HIV-1 gp41 is a Potent Inhibitor of Virus-Mediated Cell-Cell Fusion", AIDS Res. and Human Retroviruses 9:1051-1053
Wild et al., 1992, "A Synthetic Peptide Inhibitor of Human Immunodeficiency Virus Replication: Correlation between Solution Structure and Viral Inhibition", Proc. Natl. Acad. Sci USA 89:10537-10541
Wildner and Thurau, 1997, "Database Screening for Molecular Mimicry", Immunol. Today 18:252
Xu et al., 1991, "Epitope Mapping of Two Immunodominant Domains of gp41, the Transmembrane Protein of Human Immunodeficiency Virus Type 1, Using Ten Human Monoclonal Antibodies", J. Virol. 65:4832-4838
Yarchoan et al., 1989, "Phase I Study of the Administration of Recombinant Soluble CD4 (rCD4) by Continuous Infusion to Patients with AIDS or ARC", Proc. Vth Int. Conf. on AIDS, p. 564, MCP 137

UNITED STATES PATENT AND TRADEMARK OFFICE
CERTIFICATE OF CORRECTION

PATENT NO. : 6,133,418
DATED : October 17, 2000
INVENTOR(S) : Bolognesi et al.

It is certified that error appears in the above-identified patent and that said Letters Patent is hereby corrected as shown below:

Title page (cont'd),
OTHER PUBLICATIONS, please insert the following:

**Yarchoan and Broder, 1992, "Correlations between the *in vitro* and *in vivo* Activity of Anti-HIV Agents: Implications for Future Drug Development", J. Enzyme Inhib. 6:99-111**

Signed and Sealed this

Fifth Day of April, 2005

JON W. DUDAS
*Director of the United States Patent and Trademark Office*

SEQUENCE LISTING (1) GENERAL INFORMATION:

(iii) NUMBER OF SEQUENCES: 74

(2) INFORMATION FOR SEQ ID NO:1:

(i) SEQUENCE CHARACTERISTICS:
      (A) LENGTH: 36 amino acids
      (B) TYPE: amino acid
      (C) STRANDEDNESS: single
      (D) TOPOLOGY: unknown (ii) MOLECULE TYPE: peptide (xi) SEQUENCE DESCRIPTION: SEQ ID NO:1:

-continued

```
Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
                20                  25                  30

Trp Asn Trp Phe
        35
```

(2) INFORMATION FOR SEQ ID NO:2:

(i) SEQUENCE CHARACTERISTICS:
        (A) LENGTH: 36 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:2:

```
Ser Ser Glu Ser Phe Thr Leu Leu Glu Gln Trp Asn Asn Trp Lys Leu
1               5                   10                  15

Gln Leu Ala Glu Gln Trp Leu Glu Gln Ile Asn Glu Lys His Tyr Leu
                20                  25                  30

Glu Asp Ile Ser
        35
```

(2) INFORMATION FOR SEQ ID NO:3:

(i) SEQUENCE CHARACTERISTICS:
        (A) LENGTH: 36 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:3:

```
Tyr Thr Asn Thr Ile Tyr Asn Leu Leu Glu Glu Ser Gln Asn Gln Gln
1               5                   10                  15

Glu Lys Asn Glu Gln Glu Leu Leu Glu Leu Asp Lys Trp Ala Ser Leu
                20                  25                  30

Trp Asn Trp Phe
        35
```

(2) INFORMATION FOR SEQ ID NO:4:

(i) SEQUENCE CHARACTERISTICS:
        (A) LENGTH: 36 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:4:

```
Tyr Thr Gly Ile Ile Tyr Asn Leu Leu Glu Glu Ser Gln Asn Gln Gln
1               5                   10                  15

Glu Lys Asn Glu Gln Glu Leu Leu Glu Leu Asp Lys Trp Ala Asn Leu
                20                  25                  30

Trp Asn Trp Phe
        35
```

(2) INFORMATION FOR SEQ ID NO:5:

(i) SEQUENCE CHARACTERISTICS:

(A) LENGTH: 36 amino acids
           (B) TYPE: amino acid
           (C) STRANDEDNESS: single
           (D) TOPOLOGY: unknown (ii) MOLECULE TYPE: peptide (xi) SEQUENCE DESCRIPTION: SEQ ID NO:5:

Tyr Thr Ser Leu Ile Tyr Ser Leu Leu Glu Lys Ser Gln Thr Gln Gln
1               5                   10                  15

Glu Lys Asn Glu Gln Glu Leu Leu Glu Leu Asp Lys Trp Ala Ser Leu
            20                  25                  30

Trp Asn Trp Phe
            35

(2) INFORMATION FOR SEQ ID NO:6:

(i) SEQUENCE CHARACTERISTICS:
           (A) LENGTH: 36 amino acids
           (B) TYPE: amino acid
           (C) STRANDEDNESS: single
           (D) TOPOLOGY: unknown (ii) MOLECULE TYPE: peptide (xi) SEQUENCE DESCRIPTION: SEQ ID NO:6:

Leu Glu Ala Asn Ile Ser Lys Ser Leu Glu Gln Ala Gln Ile Gln Gln
1               5                   10                  15

Glu Lys Asn Met Tyr Glu Leu Gln Lys Leu Asn Ser Trp Asp Ile Phe
            20                  25                  30

Gly Asn Trp Phe
            35

(2) INFORMATION FOR SEQ ID NO:7:

(i) SEQUENCE CHARACTERISTICS:
           (A) LENGTH: 36 amino acids
           (B) TYPE: amino acid
           (C) STRANDEDNESS: single
           (D) TOPOLOGY: unknown (ii) MOLECULE TYPE: peptide (xi) SEQUENCE DESCRIPTION: SEQ ID NO:7:

Leu Glu Ala Asn Ile Ser Gln Ser Leu Glu Gln Ala Gln Ile Gln Gln
1               5                   10                  15

Glu Lys Asn Met Tyr Glu Leu Gln Lys Leu Asn Ser Trp Asp Val Phe
            20                  25                  30

Thr Asn Trp Leu
            35

(2) INFORMATION FOR SEQ ID NO:8:

(i) SEQUENCE CHARACTERISTICS:
           (A) LENGTH: 41 amino acids
           (B) TYPE: amino acid
           (C) STRANDEDNESS: single
           (D) TOPOLOGY: unknown (ii) MOLECULE TYPE: peptide (xi) SEQUENCE DESCRIPTION: SEQ ID NO:8:

Cys Gly Gly Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu

```
                    20                  25                  30
Ala Val Glu Arg Tyr Leu Lys Asp Gln
                35                  40
```

(2) INFORMATION FOR SEQ ID NO:9:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:9:

```
Leu Gln Ala Arg Ile Leu Ala Val Glu Arg Tyr Leu Lys Asp Gln Gln
1               5                  10                  15
Gln
```

(2) INFORMATION FOR SEQ ID NO:10:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:10:

```
Gln Gln Leu Leu Asp Val Val Lys Arg Gln Gln Glu Met Leu Arg Leu
1               5                  10                  15
Thr Val Trp Gly Thr Lys Asn Leu Gln Ala Arg Val Thr Ala Ile Glu
                20                  25                  30
Lys Tyr Leu Lys Asp Gln
                35
```

(2) INFORMATION FOR SEQ ID NO:11:

(i) SEQUENCE CHARACTERISTICS:
        (A) LENGTH: 35 amino acids
        (B) TYPE: amino acid
        (D) TOPOLOGY: unknown (ii) MOLECULE TYPE: peptide (xi) SEQUENCE DESCRIPTION: SEQ ID NO:11:

```
Tyr Thr Ser Leu Ile His Ser Leu Ile Glu Glu Ser Gln Asn Gln Gln
1               5                  10                  15
Glu Lys Asn Glu Gln Glu Leu Leu Glu Leu Asp Lys Trp Ala Ser Leu
                20                  25                  30
Trp Asn Trp
        35
```

(2) INFORMATION FOR SEQ ID NO:12:

(i) SEQUENCE CHARACTERISTICS:
        (A) LENGTH: 34 amino acids
        (B) TYPE: amino acid
        (D) TOPOLOGY: unknown (ii) MOLECULE TYPE: peptide (xi) SEQUENCE DESCRIPTION: SEQ ID NO:12:

```
Tyr Thr Ser Leu Ile His Ser Leu Ile Glu Glu Ser Gln Asn Gln Gln
```

```
1               5                   10                  15
Glu Lys Asn Glu Gln Glu Leu Leu Glu Leu Asp Lys Trp Ala Ser Leu
            20                  25                  30

Trp Asn (2) INFORMATION FOR SEQ ID NO:13:

(i) SEQUENCE CHARACTERISTICS:
        (A) LENGTH: 33 amino acids
        (B) TYPE: amino acid
        (D) TOPOLOGY: unknown (ii) MOLECULE TYPE: peptide (xi) SEQUENCE DESCRIPTION: SEQ ID NO:13:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp (2) INFORMATION FOR SEQ ID NO:14:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (xi) SEQUENCE DESCRIPTION: SEQ ID NO:14:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

(2) INFORMATION FOR SEQ ID NO:15:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO:15:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser
            20                  25                  30

(2) INFORMATION FOR SEQ ID NO:16:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (xi) SEQUENCE DESCRIPTION: SEQ ID NO:16:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala
```

```
             20                  25                  30
```

(2) INFORMATION FOR SEQ ID NO:17:

(i) SEQUENCE CHARACTERISTICS:
        (A) LENGTH: 29 amino acids
        (B) TYPE: amino acid
        (D) TOPOLOGY: unknown (ii) MOLECULE TYPE: peptide (xi) SEQUENCE DESCRIPTION: SEQ ID NO:17:

```
Tyr Thr Ser Leu Ile His Ser Leu Ile Glu Glu Ser Gln Asn Gln Gln
1               5                  10                  15

Glu Lys Asn Glu Gln Glu Leu Leu Glu Leu Asp Lys Trp
             20                  25
```

(2) INFORMATION FOR SEQ ID NO:18:

(i) SEQUENCE CHARACTERISTICS:
        (A) LENGTH: 28 amino acids
        (B) TYPE: amino acid
        (D) TOPOLOGY: unknown (ii) MOLECULE TYPE: peptide (xi) SEQUENCE DESCRIPTION: SEQ ID NO:18:

```
Tyr Thr Ser Leu Ile His Ser Leu Ile Glu Glu Ser Gln Asn Gln Gln
1               5                  10                  15

Glu Lys Asn Glu Gln Glu Leu Leu Glu Leu Asp Lys
             20                  25
```

(2) INFORMATION FOR SEQ ID NO:19:

(i) SEQUENCE CHARACTERISTICS:
        (A) LENGTH: 27 amino acids
        (B) TYPE: amino acid
        (D) TOPOLOGY: unknown (ii) MOLECULE TYPE: peptide (xi) SEQUENCE DESCRIPTION: SEQ ID NO:19:

```
Tyr Thr Ser Leu Ile His Ser Leu Ile Glu Glu Ser Gln Asn Gln Gln
1               5                  10                  15

Glu Lys Asn Glu Gln Glu Leu Leu Glu Leu Asp
             20                  25
```

(2) INFORMATION FOR SEQ ID NO:20:

(i) SEQUENCE CHARACTERISTICS:
        (A) LENGTH: 26 amino acids
        (B) TYPE: amino acid
        (D) TOPOLOGY: unknown (ii) MOLECULE TYPE: peptide (xi) SEQUENCE DESCRIPTION: SEQ ID NO:20:

```
Tyr Thr Ser Leu Ile His Ser Leu Ile Glu Glu Ser Gln Asn Gln Gln
1               5                  10                  15

Glu Lys Asn Glu Gln Glu Leu Leu Glu Leu
             20                  25
```

(2) INFORMATION FOR SEQ ID NO:21:

(i) SEQUENCE CHARACTERISTICS:
        (A) LENGTH: 25 amino acids (B) TYPE: amino acid
            (D) TOPOLOGY: unknown (ii) MOLECULE TYPE: peptide (xi) SEQUENCE DESCRIPTION: SEQ ID NO:21:

Tyr Thr Ser Leu Ile His Ser Leu Ile Glu Glu Ser Gln Asn Gln Gln
1               5                   10                  15

Glu Lys Asn Glu Gln Glu Leu Leu Glu
            20                  25

(2) INFORMATION FOR SEQ ID NO:22:

(i) SEQUENCE CHARACTERISTICS:
            (A) LENGTH: 24 amino acids
            (B) TYPE: amino acid
            (D) TOPOLOGY: unknown (ii) MOLECULE TYPE: peptide (xi) SEQUENCE DESCRIPTION: SEQ ID NO:22:

Tyr Thr Ser Leu Ile His Ser Leu Ile Glu Glu Ser Gln Asn Gln Gln
1               5                   10                  15

Glu Lys Asn Glu Gln Glu Leu Leu
            20

(2) INFORMATION FOR SEQ ID NO:23:

(i) SEQUENCE CHARACTERISTICS:
            (A) LENGTH: 23 amino acids
            (B) TYPE: amino acid
            (D) TOPOLOGY: unknown (ii) MOLECULE TYPE: peptide (xi) SEQUENCE DESCRIPTION: SEQ ID NO:23:

Tyr Thr Ser Leu Ile His Ser Leu Ile Glu Glu Ser Gln Asn Gln Gln
1               5                   10                  15

Glu Lys Asn Glu Gln Glu Leu
            20

(2) INFORMATION FOR SEQ ID NO:24:

(i) SEQUENCE CHARACTERISTICS:
            (A) LENGTH: 22 amino acids
            (B) TYPE: amino acid
            (D) TOPOLOGY: unknown (ii) MOLECULE TYPE: peptide (xi) SEQUENCE DESCRIPTION: SEQ ID NO:24:

Tyr Thr Ser Leu Ile His Ser Leu Ile Glu Glu Ser Gln Asn Gln Gln
1               5                   10                  15

Glu Lys Asn Glu Gln Glu
            20

(2) INFORMATION FOR SEQ ID NO:25:

(i) SEQUENCE CHARACTERISTICS:
            (A) LENGTH: 21 amino acids
            (B) TYPE: amino acid
            (D) TOPOLOGY: unknown (ii) MOLECULE TYPE: peptide (xi) SEQUENCE DESCRIPTION: SEQ ID NO:25:

Tyr Thr Ser Leu Ile His Ser Leu Ile Glu Glu Ser Gln Asn Gln Gln
1               5                   10                  15

Glu Lys Asn Glu Gln
            20

(2) INFORMATION FOR SEQ ID NO:26:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO:26:

Tyr Thr Ser Leu Ile His Ser Leu Ile Glu Glu Ser Gln Asn Gln Gln
1               5                   10                  15

Glu Lys Asn Glu
            20

(2) INFORMATION FOR SEQ ID NO:27:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (xi) SEQUENCE DESCRIPTION: SEQ ID NO:27:

Tyr Thr Ser Leu Ile His Ser Leu Ile Glu Glu Ser Gln Asn Gln Gln
1               5                   10                  15

Glu Lys Asn (2) INFORMATION FOR SEQ ID NO:28:

(i) SEQUENCE CHARACTERISTICS:
        (A) LENGTH: 18 amino acids
        (B) TYPE: amino acid
        (D) TOPOLOGY: unknown (ii) MOLECULE TYPE: peptide (xi) SEQUENCE DESCRIPTION: SEQ ID NO:28:

Tyr Thr Ser Leu Ile His Ser Leu Ile Glu Glu Ser Gln Asn Gln Gln
1               5                   10                  15

Glu Lys (2) INFORMATION FOR SEQ ID NO:29:

(i) SEQUENCE CHARACTERISTICS:
        (A) LENGTH: 17 amino acids
        (B) TYPE: amino acid
        (D) TOPOLOGY: unknown (ii) MOLECULE TYPE: peptide (xi) SEQUENCE DESCRIPTION: SEQ ID NO:29:

Tyr Thr Ser Leu Ile His Ser Leu Ile Glu Glu Ser Gln Asn Gln Gln
1               5                   10                  15

Glu (2) INFORMATION FOR SEQ ID NO:30:

(i) SEQUENCE CHARACTERISTICS:

(A) LENGTH: 16 amino acids
        (B) TYPE: amino acid
        (D) TOPOLOGY: unknown (ii) MOLECULE TYPE: peptide (xi) SEQUENCE DESCRIPTION: SEQ ID NO:30:

Tyr Thr Ser Leu Ile His Ser Leu Ile Glu Glu Ser Gln Asn Gln Gln
1               5                   10                  15

(2) INFORMATION FOR SEQ ID NO:31:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (xi) SEQUENCE DESCRIPTION: SEQ ID NO:31:

Tyr Thr Ser Leu Ile His Ser Leu Ile Glu Glu Ser Gln Asn Gln
1               5                   10                  15

(2) INFORMATION FOR SEQ ID NO:32:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:32:

Tyr Thr Ser Leu Ile His Ser Leu Ile Glu Glu Ser Gln Asn
1               5                   10

(2) INFORMATION FOR SEQ ID NO:33:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:33:

Tyr Thr Ser Leu Ile His Ser Leu Ile Glu Glu Ser Gln
1               5                   10

(2) INFORMATION FOR SEQ ID NO:34:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (xi) SEQUENCE DESCRIPTION: SEQ ID NO:34:

Tyr Thr Ser Leu Ile His Ser Leu Ile Glu Glu Ser
1               5                   10

(2) INFORMATION FOR SEQ ID NO:35:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (xi) SEQUENCE DESCRIPTION: SEQ ID NO:35:

Tyr Thr Ser Leu Ile His Ser Leu Ile Glu Glu
1               5                  10

(2) INFORMATION FOR SEQ ID NO:36:

(i) SEQUENCE CHARACTERISTICS:
            (A) LENGTH: 10 amino acids
            (B) TYPE: amino acid
            (D) TOPOLOGY: unknown (ii) MOLECULE TYPE: peptide (xi) SEQUENCE DESCRIPTION: SEQ ID NO:36:

Tyr Thr Ser Leu Ile His Ser Leu Ile Glu
1               5                  10

(2) INFORMATION FOR SEQ ID NO:37:

(i) SEQUENCE CHARACTERISTICS:
            (A) LENGTH: 9 amino acids
            (B) TYPE: amino acid
            (D) TOPOLOGY: unknown (ii) MOLECULE TYPE: peptide (xi) SEQUENCE DESCRIPTION: SEQ ID NO:37:

Tyr Thr Ser Leu Ile His Ser Leu Ile
1               5

(2) INFORMATION FOR SEQ ID NO:38:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (xi) SEQUENCE DESCRIPTION: SEQ ID NO:38:

Tyr Thr Ser Leu Ile His Ser Leu
1               5

(2) INFORMATION FOR SEQ ID NO:39:

(i) SEQUENCE CHARACTERISTICS:
            (A) LENGTH: 7 amino acids
            (B) TYPE: amino acid
            (D) TOPOLOGY: unknown (ii) MOLECULE TYPE: peptide (xi) SEQUENCE DESCRIPTION: SEQ ID NO:39:

Tyr Thr Ser Leu Ile His Ser
1               5

(2) INFORMATION FOR SEQ ID NO:40:

(i) SEQUENCE CHARACTERISTICS:
            (A) LENGTH: 6 amino acids
            (B) TYPE: amino acid
            (D) TOPOLOGY: unknown (ii) MOLECULE TYPE: peptide (xi) SEQUENCE DESCRIPTION: SEQ ID NO:40:

```
Tyr Thr Ser Leu Ile His
1               5

(2) INFORMATION FOR SEQ ID NO:41:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO:41:

Tyr Thr Ser Leu Ile
1               5

(2) INFORMATION FOR SEQ ID NO:42:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO:42:

Tyr Thr Ser Leu
1

(2) INFORMATION FOR SEQ ID NO:43:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO:43:

Trp Asn Trp Phe
1

(2) INFORMATION FOR SEQ ID NO:44:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO:44:

Leu Trp Asn Trp Phe
1               5

(2) INFORMATION FOR SEQ ID NO:45:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO:45:

Ser Leu Trp Asn Trp Phe
1               5
```

(2) INFORMATION FOR SEQ ID NO:46:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (xi) SEQUENCE DESCRIPTION: SEQ ID NO:46:

Ala Ser Leu Trp Asn Trp Phe
1               5

(2) INFORMATION FOR SEQ ID NO:47:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (xi) SEQUENCE DESCRIPTION: SEQ ID NO:47:

Trp Ala Ser Leu Trp Asn Trp Phe
1               5

(2) INFORMATION FOR SEQ ID NO:48:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO:48:

Lys Trp Ala Ser Leu Trp Asn Trp Phe
1               5

(2) INFORMATION FOR SEQ ID NO:49:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (xi) SEQUENCE DESCRIPTION: SEQ ID NO:49:

Asp Lys Trp Ala Ser Leu Trp Asn Trp Phe
1               5                   10

(2) INFORMATION FOR SEQ ID NO:50:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (xi) SEQUENCE DESCRIPTION: SEQ ID NO:50:

Leu Asp Lys Trp Ala Ser Leu Trp Asn Trp Phe
1               5                   10

(2) INFORMATION FOR SEQ ID NO:51:

(i) SEQUENCE CHARACTERISTICS:
        (A) LENGTH: 12 amino acids

```
        (B) TYPE: amino acid
        (D) TOPOLOGY: unknown (ii) MOLECULE TYPE: peptide (xi) SEQUENCE DESCRIPTION: SEQ ID NO:51:

Glu Leu Asp Lys Trp Ala Ser Leu Trp Asn Trp Phe
1               5                  10

(2) INFORMATION FOR SEQ ID NO:52:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:52:

Leu Glu Leu Asp Lys Trp Ala Ser Leu Trp Asn Trp Phe
1               5                  10

(2) INFORMATION FOR SEQ ID NO:53:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:53:

Leu Leu Glu Leu Asp Lys Trp Ala Ser Leu Trp Asn Trp Phe
1               5                  10

(2) INFORMATION FOR SEQ ID NO:54:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (xi) SEQUENCE DESCRIPTION: SEQ ID NO:54:

Glu Leu Leu Glu Leu Asp Lys Trp Ala Ser Leu Trp Asn Trp Phe
1               5                  10                  15

(2) INFORMATION FOR SEQ ID NO:55:

(i) SEQUENCE CHARACTERISTICS:
        (A) LENGTH: 16 amino acids
        (B) TYPE: amino acid
        (D) TOPOLOGY: unknown (ii) MOLECULE TYPE: peptide (xi) SEQUENCE DESCRIPTION: SEQ ID NO:55:

Gln Glu Leu Leu Glu Leu Asp Lys Trp Ala Ser Leu Trp Asn Trp Phe
1               5                  10                  15

(2) INFORMATION FOR SEQ ID NO:56:

(i) SEQUENCE CHARACTERISTICS:
        (A) LENGTH: 17 amino acids
        (B) TYPE: amino acid
        (D) TOPOLOGY: unknown (ii) MOLECULE TYPE: peptide
```

(xi) SEQUENCE DESCRIPTION: SEQ ID NO:56:

Glu Gln Glu Leu Leu Glu Leu Asp Lys Trp Ala Ser Leu Trp Asn Trp
1               5                   10                  15
Phe (2) INFORMATION FOR SEQ ID NO:57:

(i) SEQUENCE CHARACTERISTICS:
        (A) LENGTH: 18 amino acids
        (B) TYPE: amino acid
        (D) TOPOLOGY: unknown (ii) MOLECULE TYPE: peptide (xi) SEQUENCE DESCRIPTION: SEQ ID NO:57:

Asn Glu Gln Glu Leu Leu Glu Leu Asp Lys Trp Ala Ser Leu Trp Asn
1               5                   10                  15
Trp Phe (2) INFORMATION FOR SEQ ID NO:58:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (xi) SEQUENCE DESCRIPTION: SEQ ID NO:58:

Lys Asn Glu Gln Glu Leu Leu Glu Leu Asp Lys Trp Ala Ser Leu Trp
1               5                   10                  15
Asn Trp Phe (2) INFORMATION FOR SEQ ID NO:59:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO:59:

Glu Lys Asn Glu Gln Glu Leu Leu Glu Leu Asp Lys Trp Ala Ser Leu
1               5                   10                  15
Trp Asn Trp Phe
            20

(2) INFORMATION FOR SEQ ID NO:60:

(i) SEQUENCE CHARACTERISTICS:
        (A) LENGTH: 21 amino acids
        (B) TYPE: amino acid
        (D) TOPOLOGY: unknown (ii) MOLECULE TYPE: peptide (xi) SEQUENCE DESCRIPTION: SEQ ID NO:60:

Gln Glu Lys Asn Glu Gln Glu Leu Leu Glu Leu Asp Lys Trp Ala Ser
1               5                   10                  15
Leu Trp Asn Trp Phe
            20

(2) INFORMATION FOR SEQ ID NO:61:

(i) SEQUENCE CHARACTERISTICS:
        (A) LENGTH: 22 amino acids
        (B) TYPE: amino acid
        (D) TOPOLOGY: unknown (ii) MOLECULE TYPE: peptide (xi) SEQUENCE DESCRIPTION: SEQ ID NO:61:

Gln Gln Glu Lys Asn Glu Gln Glu Leu Leu Glu Leu Asp Lys Trp Ala
1               5                  10                  15

Ser Leu Trp Asn Trp Phe
            20

(2) INFORMATION FOR SEQ ID NO:62:

(i) SEQUENCE CHARACTERISTICS:
        (A) LENGTH: 23 amino acids
        (B) TYPE: amino acid
        (D) TOPOLOGY: unknown (ii) MOLECULE TYPE: peptide (xi) SEQUENCE DESCRIPTION: SEQ ID NO:62:

Asn Gln Gln Glu Lys Asn Glu Gln Glu Leu Leu Glu Leu Asp Lys Trp
1               5                  10                  15

Ala Ser Leu Trp Asn Trp Phe
            20

(2) INFORMATION FOR SEQ ID NO:63:

(i) SEQUENCE CHARACTERISTICS:
        (A) LENGTH: 24 amino acids
        (B) TYPE: amino acid
        (D) TOPOLOGY: unknown (ii) MOLECULE TYPE: peptide (xi) SEQUENCE DESCRIPTION: SEQ ID NO:63:

Gln Asn Gln Gln Glu Lys Asn Glu Gln Glu Leu Leu Glu Leu Asp Lys
1               5                  10                  15

Trp Ala Ser Leu Trp Asn Trp Phe
            20

(2) INFORMATION FOR SEQ ID NO:64:

(i) SEQUENCE CHARACTERISTICS:
        (A) LENGTH: 25 amino acids
        (B) TYPE: amino acid
        (D) TOPOLOGY: unknown (ii) MOLECULE TYPE: peptide (xi) SEQUENCE DESCRIPTION: SEQ ID NO:64:

Ser Gln Asn Gln Gln Glu Lys Asn Glu Gln Glu Leu Leu Glu Leu Asp
1               5                  10                  15

Lys Trp Ala Ser Leu Trp Asn Trp Phe
            20                  25

(2) INFORMATION FOR SEQ ID NO:65:

(i) SEQUENCE CHARACTERISTICS:
        (A) LENGTH: 26 amino acids
        (B) TYPE: amino acid
        (D) TOPOLOGY: unknown (ii) MOLECULE TYPE: peptide (xi) SEQUENCE DESCRIPTION: SEQ ID NO:65:

Glu Ser Gln Asn Gln Gln Glu Lys Asn Glu Gln Glu Leu Leu Glu Leu
1               5                  10                  15

Asp Lys Trp Ala Ser Leu Trp Asn Trp Phe
            20                  25

(2) INFORMATION FOR SEQ ID NO:66:

(i) SEQUENCE CHARACTERISTICS:
            (A) LENGTH: 27 amino acids
            (B) TYPE: amino acid
            (D) TOPOLOGY: unknown (ii) MOLECULE TYPE: peptide (xi) SEQUENCE DESCRIPTION: SEQ ID NO:66:

Glu Glu Ser Gln Asn Gln Gln Glu Lys Asn Glu Gln Glu Leu Leu Glu
1               5                  10                  15

Leu Asp Lys Trp Ala Ser Leu Trp Asn Trp Phe
            20                  25

(2) INFORMATION FOR SEQ ID NO:67:

(i) SEQUENCE CHARACTERISTICS:
            (A) LENGTH: 28 amino acids
            (B) TYPE: amino acid
            (D) TOPOLOGY: unknown (ii) MOLECULE TYPE: peptide (xi) SEQUENCE DESCRIPTION: SEQ ID NO:67:

Ile Glu Glu Ser Gln Asn Gln Gln Glu Lys Asn Glu Gln Glu Leu Leu
1               5                  10                  15

Glu Leu Asp Lys Trp Ala Ser Leu Trp Asn Trp Phe
            20                  25

(2) INFORMATION FOR SEQ ID NO:68:

(i) SEQUENCE CHARACTERISTICS:
            (A) LENGTH: 29 amino acids
            (B) TYPE: amino acid
            (D) TOPOLOGY: unknown (ii) MOLECULE TYPE: peptide (xi) SEQUENCE DESCRIPTION: SEQ ID NO:68:

Leu Ile Glu Glu Ser Gln Asn Gln Gln Glu Lys Asn Glu Gln Glu Leu
1               5                  10                  15

Leu Glu Leu Asp Lys Trp Ala Ser Leu Trp Asn Trp Phe
            20                  25

(2) INFORMATION FOR SEQ ID NO:69:

(i) SEQUENCE CHARACTERISTICS:
            (A) LENGTH: 30 amino acids
            (B) TYPE: amino acid
            (D) TOPOLOGY: unknown (ii) MOLECULE TYPE: peptide (xi) SEQUENCE DESCRIPTION: SEQ ID NO:69:

Ser Leu Ile Glu Glu Ser Gln Asn Gln Gln Glu Lys Asn Glu Gln Glu
1               5                  10                  15

```
Leu Leu Glu Leu Asp Lys Trp Ala Ser Leu Trp Asn Trp Phe
        20                  25                  30
```

(2) INFORMATION FOR SEQ ID NO:70:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO:70:

```
His Ser Leu Ile Glu Glu Ser Gln Asn Gln Gln Glu Lys Asn Glu Gln
1               5                   10                  15
Glu Leu Leu Glu Leu Asp Lys Trp Ala Ser Leu Trp Asn Trp Phe
            20                  25                  30
```

(2) INFORMATION FOR SEQ ID NO:71:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (xi) SEQUENCE DESCRIPTION: SEQ ID NO:71:

```
Ile His Ser Leu Ile Glu Glu Ser Gln Asn Gln Gln Glu Lys Asn Glu
1               5                   10                  15
Gln Glu Leu Leu Glu Leu Asp Lys Trp Ala Ser Leu Trp Asn Trp Phe
            20                  25                  30
```

(2) INFORMATION FOR SEQ ID NO:72:

(i) SEQUENCE CHARACTERISTICS:
        (A) LENGTH: 33 amino acids
        (B) TYPE: amino acid
        (D) TOPOLOGY: unknown (ii) MOLECULE TYPE: peptide (xi) SEQUENCE DESCRIPTION: SEQ ID NO:72:

```
Leu Ile His Ser Leu Ile Glu Glu Ser Gln Asn Gln Gln Glu Lys Asn
1               5                   10                  15
Glu Gln Glu Leu Leu Glu Leu Asp Lys Trp Ala Ser Leu Trp Asn Trp
            20                  25                  30
Phe
```

(2) INFORMATION FOR SEQ ID NO:73:

(i) SEQUENCE CHARACTERISTICS:
        (A) LENGTH: 34 amino acids
        (B) TYPE: amino acid
        (D) TOPOLOGY: unknown (ii) MOLECULE TYPE: peptide (xi) SEQUENCE DESCRIPTION: SEQ ID NO:73:

```
Ser Leu Ile His Ser Leu Ile Glu Glu Ser Gln Asn Gln Gln Glu Lys
1               5                   10                  15
Asn Glu Gln Glu Leu Leu Glu Leu Asp Lys Trp Ala Ser Leu Trp Asn
            20                  25                  30
Trp Phe
```

(2) INFORMATION FOR SEQ ID NO:74:

(i) SEQUENCE CHARACTERISTICS:
        (A) LENGTH: 35 amino acids
        (B) TYPE: amino acid
        (D) TOPOLOGY: unknown (ii) MOLECULE TYPE: peptide (xi) SEQUENCE DESCRIPTION: SEQ ID NO:74:

```
Thr Ser Leu Ile His Ser Leu Ile Glu Glu Ser Gln Asn Gln Gln Glu
1               5                  10                 15

Lys Asn Glu Gln Glu Leu Leu Glu Leu Asp Lys Trp Ala Ser Leu Trp
            20                  25                 30

Asn Trp Phe
        35
```